US012606795B2

(12) United States Patent  
Ma et al.

(10) Patent No.: US 12,606,795 B2  
(45) Date of Patent: Apr. 21, 2026

(54) *AKKERMANSIA MUCINIPHILA* AND PRODUCT AND APPLICATION THEREOF

(71) Applicant: Thankcome Biological Science and Technology (SuZhou) Co., Ltd., Suzhou City (CN)

(72) Inventors: Xin Ma, Suzhou City (CN); Dayong Ren, Suzhou City (CN); Yang Yu, Suzhou City (CN); Xueping Yu, Suzhou City (CN); Xin Zhao, Suzhou City (CN)

(73) Assignee: Thankcome Biological Science and Technology (SuZhou) Co., Ltd., Suzhou City (CN)

( * ) Notice: Subject to any disclaimer, the term of this patent is extended or adjusted under 35 U.S.C. 154(b) by 0 days.

(21) Appl. No.: 18/619,099

(22) Filed: Mar. 27, 2024

(65) Prior Publication Data

US 2025/0059495 A1  Feb. 20, 2025

(30) Foreign Application Priority Data

Aug. 18, 2023  (CN) .......................... 202311047614.0

(51) Int. Cl.  
*C12N 1/20* (2006.01)  
*A61K 35/74* (2015.01)

(52) U.S. Cl.  
CPC ................ *C12N 1/20* (2013.01); *A61K 35/74* (2013.01)

(58) Field of Classification Search  
CPC .......... C12N 1/20; C12N 1/205; A61K 35/74; C12R 2001/01  
See application file for complete search history.

(56) References Cited

U.S. PATENT DOCUMENTS

| | | | |
|---|---|---|---|
| 2018/0250347 A1 | 9/2018 | Cani et al. | |
| 2019/0015465 A1 | 1/2019 | Possemiers et al. | |

FOREIGN PATENT DOCUMENTS

| | | |
|---|---|---|
| CN | 116270756 A | 6/2023 |
| CN | 116421630 A | 7/2023 |
| JP | 2023-525322 A | 6/2023 |
| KR | 101799829 B1 | 11/2017 |
| KR | 102128287 B1 | 6/2020 |
| WO | 2020182916 A1 | 9/2020 |
| WO | 2023029093 A1 | 3/2023 |

OTHER PUBLICATIONS

NCBI Accession No. KT340095.1 (2 pages, Dec. 21, 2015) (Year: 2015).*  
Allen et al. (Int J Pharm Compd, 2019, 5:399, abstract; https://pubmed.ncbi.nlm.nih.gov/31513539, visited Jun. 6, 2025) (Year: 2025).*

Thornberry NA, Lazebnik Y. Caspases: enemies within. Science. Aug. 28, 1998;281(5381):1312-6. doi: 10.1126/science.281.5381. 1312. PMID: 9721091.  
Ferrier L, Mazelin L, Cenac N, Desreumaux P, Janin A, Emilie D, Colombel JF, Garcia-Villar R, Fioramonti J, Bueno L. Stress-induced disruption of colonic epithelial barrier: role of interferon-gamma and myosin light chain kinase in mice. Gastroenterology. Sep. 2003;125(3):795-804. doi: 10.1016/s0016-5085(03)01057-6. PMID: 12949725.  
Zingoni A, Sornasse T, Cocks BG, Tanaka Y, Santoni A, Lanier LL. Cross-talk between activated human NK cells and CD4+ T cells via OX40-OX40 ligand interactions. J Immunol. Sep. 15, 2004;173(6):3716-24. doi: 10.4049/jimmunol.173.6.3716. PMID: 15356117.  
Li J, Yuan J. Caspases in apoptosis and beyond. Oncogene. Oct. 20, 2008;27(48):6194-206. doi: 10.1038/onc.2008.297. PMID: 18931687.  
Drury LJ, Wendt MK, Dwinell MB. CXCL12 chemokine expression and secretion regulates colorectal carcinoma cell anoikis through Bim-mediated intrinsic apoptosis. PLoS One. Sep. 22, 2010;5(9):e12895. doi: 10.1371/journal.pone.0012895. PMID: 20877573; PMCID: PMC2943927.  
Huang G, Chen X, Cai Y, Wang X, Xing C. miR-20a-directed regulation of BID is associated with the TRAIL sensitivity in colorectal cancer. Oncol Rep. Jan. 2017;37(1):571-578. doi: 10.3892/or.2016.5278. Epub Nov. 28, 2016. PMID: 28004114.  
Jayaraman , P.-S., Wadey, K., George, S., & Gaston, K. (2018). Phosphorylation of PRH/HHEX by Protein Kinase CK2 regulates cellproliferation and cell migration in diverse cell types. In Geneexpression and regulation in mammalian cells: transcription fromgeneral aspects (pp. 237-255). InTechPublication.https://doi.org/10.5772/intechopen.70352.  
Minxuan, Xu; Sun, Yan; Dai, Xianling; Zhan, Jianxia; Long, Tingting; Xiong, Mingxing; Li, Huanhuan; Kuang, Qin; Tang, Tingting; Qin, Yuting; Chenxu, Ge; Jun, Tan (2019). Fisetin attenuates high fat diet-triggered hepatic lipid accumulation: A mechanism involving liver inflammation overload associated TACE/TNF-α pathway. Journal of Functional Foods, 53(), 7-21. doi:10.1016/j.jff.2018.12.007.  
Park JS, Choi J, Hwang SH, Kim JK, Kim EK, Lee SY, Lee BI, Park SH, Cho ML. Cottonseed Oil Protects Against Intestinal Inflammation in Dextran Sodium Sulfate-Induced Inflammatory Bowel Disease. J Med Food. Jul. 2019;22(7):672-679. doi: 10.1089/jmf.2018.4323. Epub May 21, 2019. PMID: 31112045.  
Pan Y, Ning Y, Hu J, Wang Z, Chen X, Zhao X. The Preventive Effect of Lactobacillus plantarum ZS62 on DSS-Induced IBD by Regulating Oxidative Stress and the Immune Response. Oxid Med Cell Longev. Oct. 27, 2021;2021:9416794. doi: 10.1155/2021/9416794. PMID: 34745426; PMCID: PMC8566036.  
(2001). M100-S11, Performance standards for antimicrobial susceptibility testing. , 23(6), 1-. doi:10.1016/s0196-4399(01)88009-0.

* cited by examiner

Primary Examiner — David Steadman  
Assistant Examiner — Joseph R Spangler  
(74) Attorney, Agent, or Firm — Fox Rothschild LLP

(57) ABSTRACT

The disclosure belongs to the field of microorganisms, and in particular relates to a strain of *Akkermansia muciniphila* and a product and application thereof. The *A. muciniphila* is AKK PROBIO, with a preservation number of CGMCC No. 20955. AKK PROBIO of the disclosure has good tolerance, high safety, wide indications, and a good therapeutic effect, can prevent and treat diseases such as colitis, colorectal carcinoma, Alzheimer's disease, and gouty arthritis, and has very good clinical application prospects.

20 Claims, 21 Drawing Sheets

Specification includes a Sequence Listing.

Fig. 3E                                      Fig. 3F

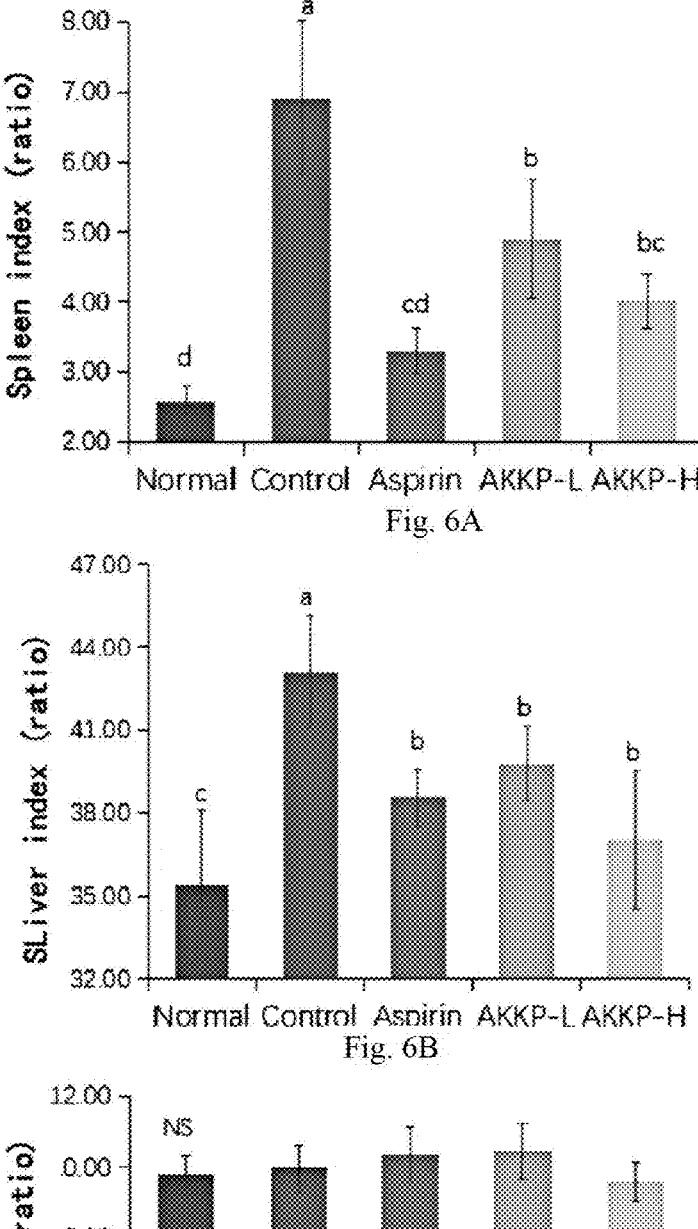
Fig. 6A
Fig. 6B
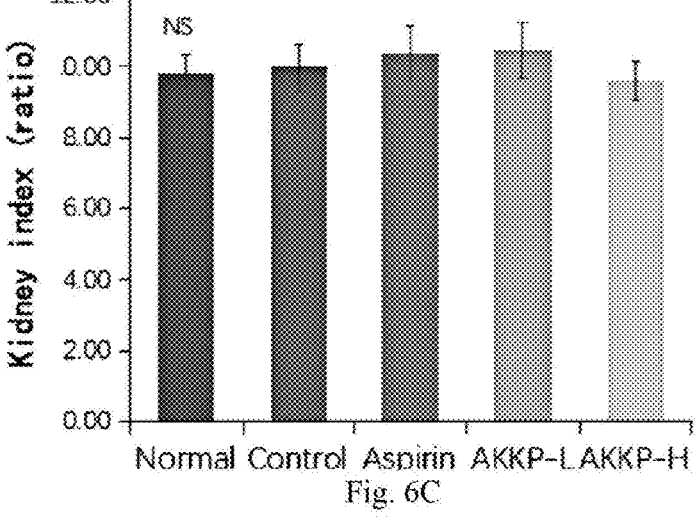
Fig. 6C
Fig. 6

Fig. 7A     Normal          Fig. 7B     Control

Fig. 7C     Aspirin          Fig. 7D     AKKP-L

Fig. 7E     AKKP-H

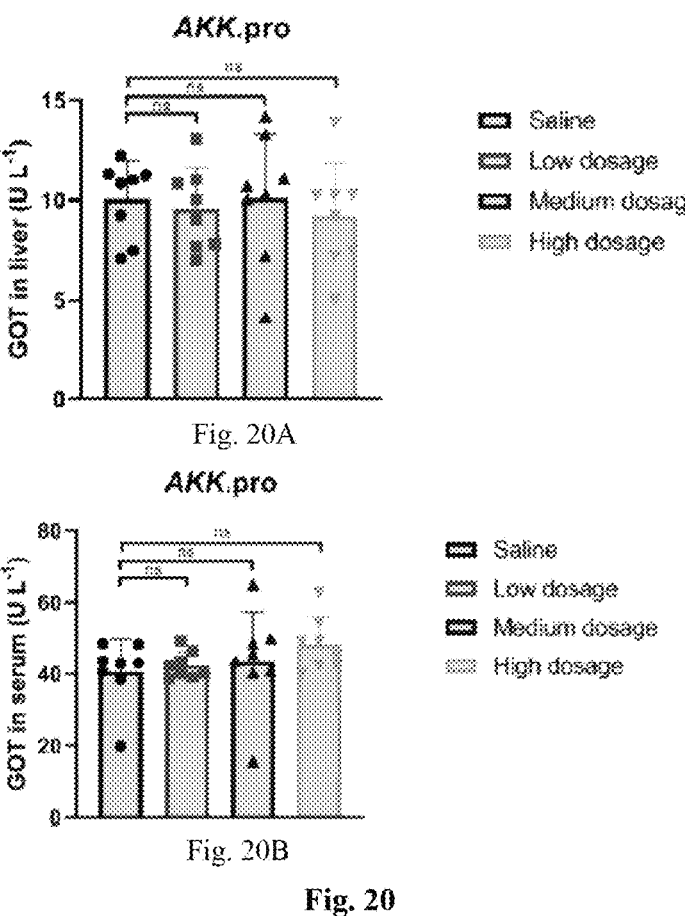
Fig. 20A
Fig. 20B
Fig. 20
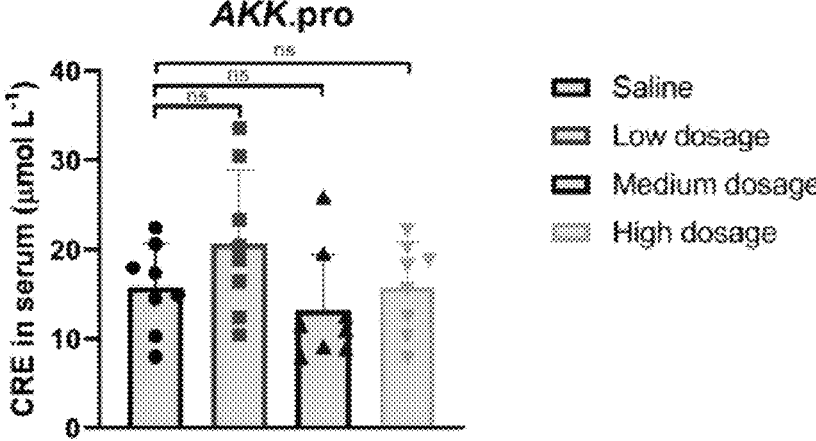
Fig. 21

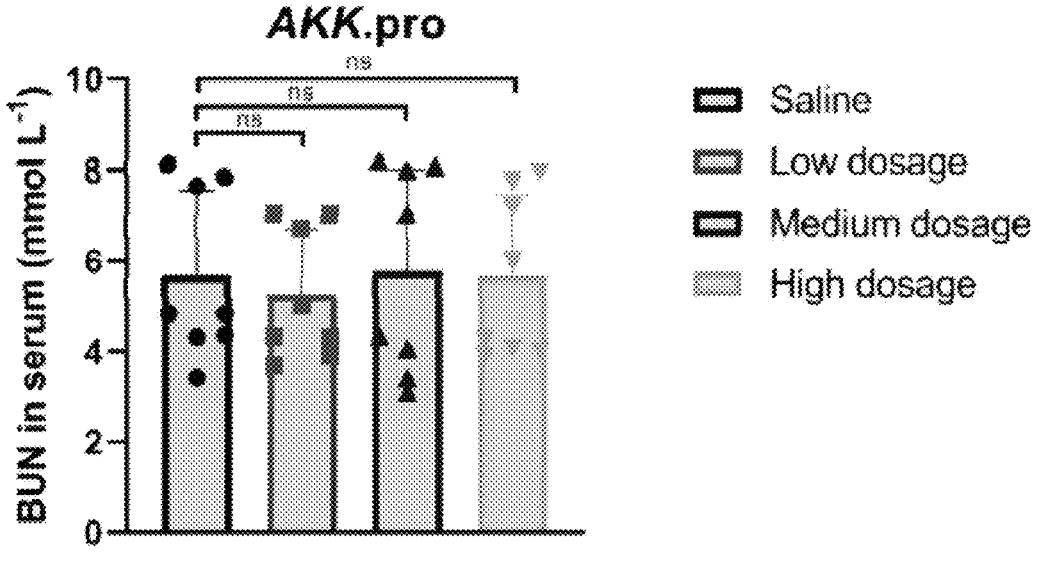
Fig. 22
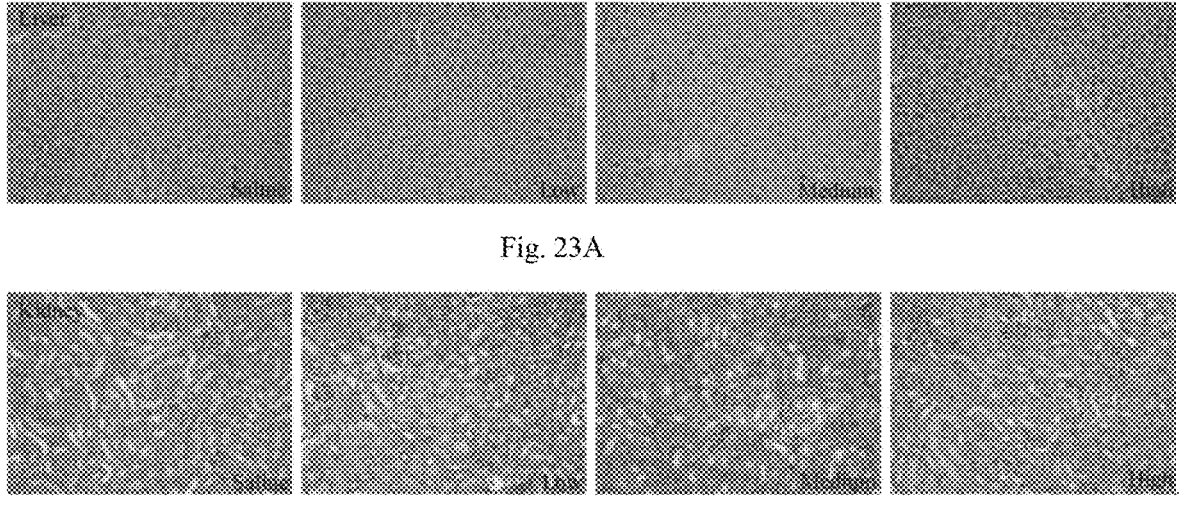
Fig. 23A
Fig. 23B
Fig. 23

SEQUENCE LISTING

```
Sequence total quantity: 19
SEQ ID NO: 1            moltype = DNA   length = 1362
FEATURE                 Location/Qualifiers
source                  1..1362
                        mol_type = genomic DNA
                        organism = Akkermansia muciniphila
SEQUENCE: 1
aacgagagaa ttgctagctt gctaataatt ctctagtggc gcacgggtga gtaacacgtg   60
agtaacctgc ccccgagagc gggatagccc tgggaaactg ggattaatac cgcatagtat  120
cgaaagatta aagcagcaat gcgcttgggg atgggctcgc ggcctattag ttagttggtg  180
aggtaacggc tcaccaaggc gatgacgggt agccggtctg agaggatgtc cggccacact  240
ggaactgaga cacggtccag acacctacgg gtggcagcag tcgagaatca ttcacaatgg  300
gggaaaccct gatggtgcga cgccgcgtgg gggaatgaag gtcttcggat tgtaaacccc  360
tgtcatgtgg gagcaaatta aaaagatagt accacaagag gaagagacgg ctaactctgt  420
gccagcagcc gcggtaatac agaggtctca agcgttgttc ggaatcactg ggcgtaaagc  480
gtgcgtaggc tgtttcgtaa gtcgtgtgtg aaaggcgcgg gctcaacccg cggacggcac  540
atgatactgc gagactagag taatggaggg ggaaccggaa ttctcggtgt agcagtgaaa  600
tgcgtagata tcgagaggaa cactcgtggc gaaggcgggt tcctggacat taactgacgc  660
tgaggcacga aggccagggg agcgaaaggg attagatacc cctgtagtcc tggcagtaaa  720
cggtgcacgc ttggtgtgcg gggaatcgac cccctgcgtg ccggagctaa cgcgttaagc  780
gtgccgcctg gggagtacgg tcgcaagatt aaaactcaaa gaaattgacg gggacccgca  840
caagcggtgg agtatgtggc ttaattcgat gcaacgcgaa gaaccttacc tgggcttgac  900
atgtaatgaa caacatgtga aagcatgcga ctcttcggag gcgttacaca ggtgctgcat  960
ggccgtcgtc agctcgtgtc gtgagatgtt tggttaagtc cagcaacgag cgcaacccct 1020
gttgccagtt accagcacgt gaaggtgggg actctggcga gactgcccag atcaactggg 1080
aggaaggtgg ggacgacgtc aggtcagtat ggcccttatg cccagggctg cacacgtact 1140
acaatgccca gtacagaggg ggccgaagcc gcgaggcgga ggaaatccta aaaactgggc 1200
ccagttcgga ctgtaggctg caacccgcct acacgaagcc ggaatcgcta gtaatggcgc 1260
atcagctacg gcgccgtgaa tacgttcccg ggtcttgtac acaccgcccg tcacatcatg 1320
gaagccggtc gcacccgaag tatctgaagc caaccgcaag ga                     1362

SEQ ID NO: 2            moltype = DNA   length = 19
FEATURE                 Location/Qualifiers
source                  1..19
                        mol_type = other DNA
                        organism = synthetic construct
SEQUENCE: 2
agagtttgat cctggctca                                                 19

SEQ ID NO: 3            moltype = DNA   length = 19
FEATURE                 Location/Qualifiers
```

-continued

```
source                  1..19
                        mol_type = other DNA
                        organism = synthetic construct
SEQUENCE: 3
ggttaccttg ttacgactt                                            19

SEQ ID NO: 4            moltype = DNA   length = 20
FEATURE                 Location/Qualifiers
source                  1..20
                        mol_type = other DNA
                        organism = synthetic construct
SEQUENCE: 4
tgtcagtcat cgcccatgtg                                           20

SEQ ID NO: 5            moltype = DNA   length = 21
FEATURE                 Location/Qualifiers
source                  1..21
                        mol_type = other DNA
                        organism = synthetic construct
SEQUENCE: 5
catccttgcg agtgtcagtg a                                         21

SEQ ID NO: 6            moltype = DNA   length = 20
FEATURE                 Location/Qualifiers
source                  1..20
                        mol_type = other DNA
                        organism = synthetic construct
SEQUENCE: 6
agaggggatt tcgattccgc                                           20

SEQ ID NO: 7            moltype = DNA   length = 23
FEATURE                 Location/Qualifiers
source                  1..23
                        mol_type = other DNA
                        organism = synthetic construct
SEQUENCE: 7
cctgtgggta ggatttcttg ttc                                       23

SEQ ID NO: 8            moltype = DNA   length = 21
FEATURE                 Location/Qualifiers
source                  1..21
                        mol_type = other DNA
                        organism = synthetic construct
SEQUENCE: 8
tggcatcccc gaatatgatg a                                         21

SEQ ID NO: 9            moltype = DNA   length = 22
FEATURE                 Location/Qualifiers
source                  1..22
                        mol_type = other DNA
                        organism = synthetic construct
SEQUENCE: 9
tgacagtagg ataggtcttc cg                                        22

SEQ ID NO: 10           moltype = DNA   length = 20
FEATURE                 Location/Qualifiers
source                  1..20
                        mol_type = other DNA
                        organism = synthetic construct
SEQUENCE: 10
actgccggga tggctactat                                           20

SEQ ID NO: 11           moltype = DNA   length = 21
FEATURE                 Location/Qualifiers
source                  1..21
                        mol_type = other DNA
                        organism = synthetic construct
SEQUENCE: 11
tctggattcg ctggctaatg g                                         21

SEQ ID NO: 12           moltype = DNA   length = 21
FEATURE                 Location/Qualifiers
source                  1..21
                        mol_type = other DNA
                        organism = synthetic construct
SEQUENCE: 12
gacatcgcat cggctcttag a                                         21

SEQ ID NO: 13           moltype = DNA   length = 21
```

-continued

```
FEATURE                 Location/Qualifiers
source                  1..21
                        mol_type = other DNA
                        organism = synthetic construct
SEQUENCE: 13
aacggtcacg gtgtacttct g                                          21

SEQ ID NO: 14           moltype = DNA   length = 21
FEATURE                 Location/Qualifiers
source                  1..21
                        mol_type = other DNA
                        organism = synthetic construct
SEQUENCE: 14
tcctggtaca tcgagacctt g                                          21

SEQ ID NO: 15           moltype = DNA   length = 21
FEATURE                 Location/Qualifiers
source                  1..21
                        mol_type = other DNA
                        organism = synthetic construct
SEQUENCE: 15
aagtcccttt cgcagaaaca g                                          21

SEQ ID NO: 16           moltype = DNA   length = 20
FEATURE                 Location/Qualifiers
source                  1..20
                        mol_type = other DNA
                        organism = synthetic construct
SEQUENCE: 16
ccagtcacgc accatctttg                                            20

SEQ ID NO: 17           moltype = DNA   length = 23
FEATURE                 Location/Qualifiers
source                  1..23
                        mol_type = other DNA
                        organism = synthetic construct
SEQUENCE: 17
gtccatctcg tttctaacca agt                                        23

SEQ ID NO: 18           moltype = DNA   length = 20
FEATURE                 Location/Qualifiers
source                  1..20
                        mol_type = other DNA
                        organism = synthetic construct
SEQUENCE: 18
cccggagata cggattgcac                                            20

SEQ ID NO: 19           moltype = DNA   length = 20
FEATURE                 Location/Qualifiers
source                  1..20
                        mol_type = other DNA
                        organism = synthetic construct
SEQUENCE: 19
gcctcgcggt aatcatttgc                                            20
```

AKKERMANSIA MUCINIPHILA AND PRODUCT AND APPLICATION THEREOF

The contents of the electronic sequence listing (18619099_Sequence_listing.xml; Size: 19,263 bytes; and Date of Creation: Mar. 14, 2024) is herein incorporated by reference.

TECHNICAL FIELD

The disclosure belongs to the field of microorganisms, and in particular relates to a strain of *Akkermansia muciniphila* and a product and application thereof.

BACKGROUND

All microbial life that lives in or on specific parts of a human body is collectively called a human microbiome. The DNA sequencing technology has promoted a deeper analysis of a microbiome of gut, skin, urogenital tract, and lungs, revealing the role of microbes residing in symbiosis with the surface of mucosa of a host. The composition and activity of the microbiome have significant metabolic, nutritional, and immune effects on the host. The microbiome evolves within the host from birth, and makes a fine adjustment constantly to maintain a homeostatic balance with the immune system of the host. This evolution is influenced by host factors (such as adaptability and innate immune response), external factors (such as diet, drug and toxin exposure), and diseases.

Both types and numbers of gastrointestinal microorganisms account for a relatively large proportion of the human body, where approximately 100 trillion microorganisms reside in the intestine. These microorganisms are highly adapted to survive in a complex community structure, and the microbiome varies greatly among different individuals. This variability is even more significant when patients with a disease (such as an inflammatory bowel disease) are compared to healthy individuals, indicating that an imbalance (i.e., ecological disturbance) of certain microbes within the microbiome may contribute to abnormal inflammatory and metabolic reactions. Regulating the composition of the gastrointestinal microorganisms may have a certain therapeutic effect on some diseases. For example, certain probiotics such as *Lactobacillus* and Bifidobacteria have been administered orally to treat respiratory tract inflammation in murine models.

*Akkermansia muciniphila* (*A. muciniphila*, AKK) is an oval-shaped Gram-negative bacterium isolated from human feces. It is a symbiotic bacterium in the human gut and can survive by relying on mucin in an intestinal mucus layer. Symbiotic bacteria in the human body can provide a beneficial help via various pathways, including helping to digest foods and forming a healthy immune system. The *A. muciniphila*, as a gut symbiotic bacterium, has been found to have multiple functions.

For example, an *A. muciniphila* product for preventing and treating tumors and application thereof are disclosed in the Chinese patent with the application No. of CN202310386672.X, it includes at least *A. muciniphila*. The *A. muciniphila* includes one or two of AM06 and AM02. Through a large number of experiments, it has been proven that viable bacteria, inactivated bacteria, and bacterial cell lysate of the *A. muciniphila* have an effect of preventing and treating tumors, and when the product is combined with other immune checkpoint inhibitors such as a PD-1 antibody or a CTLA-4 antibody, the anti-tumor effect of the immune checkpoint inhibitors can be significantly enhanced. But this strain has a little tumor suppression effect, and a relatively low tumor suppression rate.

For another example, a novel *A. muciniphila* AK32 strain and a composition containing the same for preventing and treating intestinal injury are disclosed in the patent with the application No. of JP2022568622. The *A. muciniphila* AK32 strain not only increases the height of an intestinal crypt and the number of goblet cells in an animal model, but also promotes intestinal epithelial cell proliferation-related gene expression, and is effective in regeneration and growth of intestinal tissue and organoids. Therefore, the *A. muciniphila* AK32 strain is effective for production of foods and drugs, intestinal regulation, probiotics and the like. However, the actual degree of improvement by the *A. muciniphila* AK32 strain is relatively low, and its scope of clinical application is relatively narrow.

Various other indications for the *A. muciniphila*, such as obesity, diabetes, cardiovascular metabolic diseases, amyotrophic lateral sclerosis, cognitive dysfunction are further disclosed in the prior art. A mechanism of the *A. muciniphila* in treatment of related diseases has also been researched in some prior arts. However, the *A. muciniphila* in the prior art, as mentioned earlier, still has a lot of room for improvement in the treatment of the related diseases, and continuous expansion of a germplasm bank of related strains is also beneficial for later research on disease type extension. In addition, strains in the prior art have relatively single functions. The *A. muciniphila* that integrates multiple therapeutic effects is screened out and can be better and more convenient to serve clinical practice.

SUMMARY

In order to solve the above problems, healthy human fecal samples are isolated and screened to obtain a strain of *A. muciniphila* in the disclosure. Multiple performance tests are conducted on this strain, and research on multiple application directions is carried out in order to expand the microorganism germplasm bank.

In one aspect, the disclosure provides a strain of *A. muciniphila*.

The *A. muciniphila* is AKK PROBIO, with a preservation number of CGMCC No. 20955, and was deposited on Oct. 26, 2020 in the China General Microbiological Culture Collection Center.

The *A. muciniphila* of the disclosure is isolated using a mucin medium.

The *A. muciniphila* has a 16S sequence of SEQ ID NO. 1.

The *A. muciniphila* is subjected to anaerobic culture at 37° C. in a BHI medium for 7 d, and from plate morphology, colonies are light yellow, round, and semi-transparent, and have a moist surface, and neat edges. The *A. muciniphila* is subjected to anaerobic culture at 37° C. in the BHI medium for 4 d, and a microscopic examination shows that bacterial cells are rod-shaped, with a size ranging from 0.5 to 0.9 $\mu m \times 0.7$ to 3.8 $\mu m$, arranged singly or in pairs, and Gram-negative.

The AKK PROBIO of the disclosure is also referred to as AKK. pro or AKKP in some expressions.

In another aspect, the disclosure provides a culture method for the aforementioned *A. muciniphila*.

The culture method at least includes inoculating the aforementioned *A. muciniphila* into a medium and performing culture.

Specifically, the inoculation includes but is not limited to any one or more of: plate streaking, inoculation on agar slant, pour culture, punch inoculation, or liquid inoculation.

The inoculum size of the inoculation may be 0.1% to 20%, and in some cases, the inoculum size may also be higher or lower. Specifically, the inoculum size may be 1% to 20%, 2% to 20%, 1% to 15%, 1% to 10%, 1% to 5%, 1% to 8%, 5% to 15%, 5% to 10%, 5% to 8%, 8% to 10%, 8% to 15%, 5% to 12%, and 2% to 7%.

Specifically, the medium may be a solid medium, a semi-solid medium, or a liquid medium, and more specifically, it may be any suitable medium already disclosed in the prior art, or a medium that is further improved on the basis of the medium disclosed in the prior art to improve strain performance, or a medium that is not disclosed in the prior art but can be used for culture of the aforementioned *A. muciniphila*.

The medium includes but is not limited to: one or more of brain heart infusion, mucin, amino acid or its salts, glucose or its derivatives, vitamins, calcium chloride, magnesium chloride, disodium phosphate, sodium chloride, dipotassium phosphate, sodium bicarbonate, sodium sulfide, yeast extract, beef extract, peptone, bile, and animal blood.

The animal blood includes but is not limited to bovine blood, sheep blood, swine blood, chicken blood, and duck blood, preferably the sheep blood.

Preferably, the medium is a BHI medium, which may be in a solid or liquid form. The medium may be a finished medium or a self prepared medium in which ingredients can be regulated routinely as needed.

When the BHI medium is a solid medium, it includes agar, and further includes but is not limited to any one or more of: brain heart extract, peptone, dehydrated calf brain infusion powder, dehydrated beef heart infusion powder, glucose, and an inorganic salt; preferably, the inorganic salt may be any one or both of sodium chloride or disodium hydrogen phosphate.

When the BHI medium is a liquid medium, it includes but is not limited to any one or more of: brain heart extract, peptone, dehydrated calf brain infusion powder, dehydrated beef heart infusion powder, glucose, and an inorganic salt; preferably inorganic salt may be any one or both of sodium chloride or disodium hydrogen phosphate.

The medium may further include mucin.

In some expressions, the medium may include a basic medium and additives, where the basic medium may be a common universal medium in the prior art, such as a BHI medium, the additives may be other common or uncommon components in the art, such as animal blood, and a volume ratio of the animal blood to the medium may be 1% to 10%, specifically 1% to 5%, 5% to 10%, 1% to 8%, 2% to 10%, 4% to 8%, 5% to 8% preferably 5% to 10%, further preferably 5% or 10%. In some embodiments of the disclosure, the medium includes a BHI medium and sheep blood, where a volume ratio of the sheep blood to the BHI medium may be 1% to 10%, specifically 1% to 5%, 5% to 10%, 1% to 8%, 2% to 10%, 4% to 8%, 5% to 8%, preferably 5% to 10%, further preferably 5% or 10%.

Culture conditions for the *A. muciniphila* provided by the disclosure include temperature, oxygen content, and in some cases may further include light, carbon dioxide content, pH, humidity, stirring conditions, ventilation conditions, oscillation conditions, medium replacement conditions, culture days, resistance conditions and the like.

Preferably, the temperature in the culture conditions may be 35° C. to 40° C., specifically 35° C. to 39° C., 35° C. to 38° C., 35° C. to 37° C., 35° C. to 36° C., 36° C. to 40° C., 36° C. to 39° C., 36° C. to 38° C., 36° C. to 37° C., 37° C. to 40° C., 37° C. to 39° C., 37° C. to 38° C., 38° C. to 40° C., 38° C. to 39° C., 39° C. to 40° C., 36.5° C. to 38.5° C., 35.5° C. to 37.5° C., 37° C. to 38.5° C., or 37° C. to 37.5° C. Further preferably 36° C. to 38° C. and further 37° C.

Preferably, the culture is anaerobic culture, and the oxygen content in the culture conditions may be 0% to 8%, specifically 0% to 7%, 0% to 6%, 0% to 5%, 0% to 4%, 0% to 3%, 0% to 2%, 0% to 1%, 0% to 5.5%, 0% to 3.5%, 0% to 2.5%, 0% to 0.5%, 1% to 8%, 1% to 5%, 1% to 2%, or 0.5% to 2%.

In yet another aspect, the disclosure provides a preparation of the aforementioned *A. muciniphila*.

The preparation includes but is not limited to: one or more of viable bacteria, dead bacteria, fermented broth, fermented broth supernatant, fermented broth precipitates, freeze-dried powder, cell lysate, or secretions.

The preparation can be prepared from a culture obtained by the aforementioned culture method.

As an example, the viable bacteria may be viable cells obtained from the aforementioned culture by centrifugation, filtration or otherwise.

As an example, the viable bacteria may be inactivated bacterial cells, where the inactivation includes but is not limited to: one or more of high-temperature inactivation, radiation inactivation, or chemical inactivation.

Specifically, the high-temperature inactivation may be dry heat inactivation or wet heat inactivation; the radiation inactivation may be light radiation or ionizing radiation, the light radiation may be ultraviolet or infrared radiation, and the ionizing radiation includes but is not limited to microwave radiation; and the chemical inactivation includes but is not limited to gas sterilization or liquid sterilization, where the gas sterilization is carried out using a gaseous bactericide such as ozone or formaldehyde, and the liquid sterilization is completed using a liquid bactericide.

As an example, the fermented broth can be obtained through the aforementioned culture method, where according to the general knowledge in the art, the culture method includes inoculating a strain into a liquid medium and performing culture under certain conditions to obtain a liquid culture, i.e., the fermented broth.

As an example, the fermented broth supernatant or precipitate is obtained by centrifugal separation of the aforementioned fermented broth. In some cases, the fermented broth supernatant or precipitate includes bacterial cells of the *A. muciniphila*. The centrifugal separation conditions may be high-speed centrifugation or low-speed centrifugation, and may be room temperature, low temperature, or high temperature.

As an example, the freeze-dried powder is obtained by freeze-drying the aforementioned culture solution. The freeze-dried powder generally further includes a freeze-dried protectant. The freeze-drying protectant includes but is not limited to: a pH buffer, filler, sugars, non-ionic surfactants, ligands and the like. The pH buffer includes but is not limited to any one or more of Tris, amino acid or its salts, citric acid or its salts, acetic acid or its salts. The filler includes but is not limited to any one or more of mannitol, glycine, or bovine serum albumin. The sugars may be disaccharides, such as any one or more of sucrose or trehalose. The non-ionic surfactants include but are not limited to Tween, where the Tween may be Tween-20, Tween-60, Tween-80 and the like. The freeze-dried protectants may further include an antioxidant and the like. The freeze-dried protectants may further include albumin, polyethylene glycol and the like.

As an example, the cell lysate can be obtained by lysis of bacterial cells obtained by culturing the aforementioned culture. The lysis may be either physical lysis or chemical lysis. The physical lysis includes but is not limited to: grinding, ultrasonic crushing and the like. The chemical lysis includes but is not limited to: chemical reagent lysis and enzymolysis, where the enzymolysis may be enzymolysis with hydrolase or oxidase. The lysis can also cause cells to rupture themselves by increasing pressure in the cells.

As an example, the secretions may be proteins, sugars, or lipids.

In still another aspect, the disclosure provides application of the aforementioned *A. muciniphila* or preparation to preparation of a food, a medicine, a health-care product, a microbial agent, a food additive, a health-care product additive or a pharmaceutical raw material.

The medicine is used for preventing or treating tumors or tumor complications.

The tumors include but are not limited to solid tumors or non-solid tumors.

The solid tumors include but are not limited to motor system tumors, digestive system tumors, respiratory system tumors, nervous system tumors, urinary system tumors, reproductive system tumors, and/or endocrine system tumors.

Preferably, the tumors include but are not limited to: any one or more of breast carcinoma, lung carcinoma, colorectal carcinoma, pancreatic carcinoma and melanoma.

The medicine can also be used for preventing or treating diseases such as obesity, diabetes, cardiovascular diseases, inflammation, amyotrophic lateral sclerosis, and Alzheimer's disease, or complications of the above diseases.

The inflammation includes but is not limited to acute inflammation or chronic inflammation. The inflammation includes but is not limited to any one or more of arthritis, gastroenteritis, hepatitis, fasciitis, nephritis, stomatitis, cystitis, pelvic inflammation, cervicitis, keratitis, conjunctivitis, rhinitis, tympanitis, pneumonia, and tracheitis.

Under some classification, the medicine can be used for preventing or treating a cognitive dysfunction, such as the aforementioned Alzheimer's disease.

The health-care product can be used for maintaining intestinal flora balance, maintaining a body shape, maintaining blood pressure, maintaining blood lipids, protecting memory, resisting oxidation, regulating metabolism, and regulating immunity.

In yet another aspect, the disclosure provides a product including the aforementioned *A. muciniphila* or preparation.

The product includes but is not limited to a food, a medicine, a health-care product, a microbial agent, a food additive, a health-care product additive or a pharmaceutical raw material.

The product preferably is the medicine, where the medicine further includes a pharmaceutically acceptable excipient.

The pharmaceutically acceptable excipient includes but is not limited to: any one or more of an excipient, a stabilizer, a diluent, an adhesive, a preservative, a lubricant, and an antioxidant. Preferably, the medicine is in an internal or external dosage form.

The internal dosage form includes but is not limited to any one of a tablet, powder, a granule, a capsule, oral liquid, pulvis, a pill, syrup, or an effervescing agent.

The external dosage form includes but is not limited to any one of emulsion, ointment, spray, liniment, suppository, lotion, a foaming agent and a gelling agent.

Preferably, the viable count of the *A. muciniphila* in the medicine is not less than $1 \times 10^8$ CFU/g or $1 \times 10^8$ CFU/mL.

Further preferably, the viable count of the *A. muciniphila* in the medicine is not less than $1 \times 10^9$ CFU/g or $1 \times 10^9$ CFU/mL. Specifically, the viable count of the *A. muciniphila* is not less than $1 \times 10^9$ CFU/g or $1 \times 10^9$ CFU/mL, such as not less than $1 \times 10^9$ CFU/g (CFU/mL), $2 \times 10^9$ CFU/g (CFU/mL), $3 \times 10^9$ CFU/g (CFU/mL), $4 \times 10^9$ CFU/g (CFU/mL), $5 \times 10^9$ CFU/g (CFU/mL), $6 \times 10^9$ CFU/g (CFU/mL), $7 \times 10^9$ CFU/g (CFU/mL), $8 \times 10^9$ CFU/g (CFU/mL), $9 \times 10^9$ CFU/g (CFU/mL), $10 \times 10^9$ CFU/g, and other point values within the range of this numerical value can be selected.

Preferably, the viable count of the *A. muciniphila* in the medicine is $1 \times 10^8$ to $1 \times 10^{12}$ CFU/g or $1 \times 10^8$ to $1 \times 10^{12}$ CFU/mL. Specifically, the viable count may be $1 \times 10^8$ to $1 \times 10^9$ CFU/g (CFU/mL), $1 \times 10^8$ to $1 \times 10^{10}$ CFU/g (CFU/mL), $1 \times 10^8$ to $1 \times 10^{11}$ CFU/g (CFU/mL), $1 \times 10^9$ to $1 \times 10^{12}$ CFU/g (CFU/mL), $1 \times 10^9$ to $1 \times 10^{11}$ CFU/g (CFU/mL), $1 \times 10^9$ to $1 \times 10^{10}$ CFU/g (CFU/mL), $1 \times 10^{10}$ to $1 \times 10^{12}$ CFU/g (CFU/mL), $1 \times 10^{10}$ to $1 \times 10^{11}$ CFU/g (CFU/mL), $1 \times 10^{11}$ to $1 \times 10^{12}$ CFU/g (CFU/mL), $5 \times 10^8$ to $1 \times 10^{12}$ CFU/g (CFU/mL), $8 \times 10^8$ to $1 \times 10^{12}$ CFU/g (CFU/mL), $7 \times 10^9$ to $2 \times 10^{11}$ CFU/g (CFU/mL) or $9 \times 10^{10}$ to $6 \times 10^{11}$ CFU/g (CFU/mL).

Further preferably, the viable count of the *A. muciniphila* in the medicine is $1 \times 10^9$ to $1 \times 10^{12}$ CFU/g or $1 \times 10^9$ to $1 \times 10^{12}$ CFU/mL.

Those skilled in the art can combine excipients in the related art with the *A. muciniphila* or the preparation thereof provided in the disclosure according to actual application, which can be achieved through routine screening by those skilled in the art.

The disclosure has the following advantageous effects:

A strain of *A. muciniphila*, AKK PROBIO, is obtained by screening in the disclosure, where the hydrophobicity of the strain reaches 30% and above at 60 min, and the auto-aggregation tends to stabilize at around 52% at 20 h. The strain has good tolerance to gastrointestinal juice and tolerance to bile salt and has a survival rate of around 85% in gastric juice at 240 min and 80% and above in the intestinal juice at 240 min.

AKK PROBIO has preventive and therapeutic effects on various diseases on the basis of its relatively high safety.

AKK PROBIO has a significant regulatory effect on colorectal carcinoma in mice, can alleviate AOM/DSS-induced body weight loss, reduction in colorectum length, and rise in spleen and liver indices of the mice to a certain extent, and effectively reduces the tumor number and the degree of rectum tissue damage in CRC mice. It can significantly reduce expressions of pro-inflammatory factors IL-1β, IL-6, IFN-γ, iNOS and NF-κB in the serum of the mouse. At the genetic level, it can significantly down-regulate mRNA expressions of p50, p52, p65, and IκBβ in colon tissue, up-regulate mRNA expressions of caspase-9, Bid and Bim in colon tissue, reduce the degree of intestinal inflammation, and influence occurrence and development of the colorectal carcinoma.

AKK PROBIO has an effect of alleviating Alzheimer's disease in mice. After 4 consecutive days of Morris water maze training, mice taking AKK PROBIO have a shortened escape latency, and a path to finding a platform is significantly shortened. The purpose of clearing Aβ is achieved by up-regulating the levels of Aβ degrading enzyme IDE and anti-inflammatory factors IL-4 and IL-10, thereby alleviating Alzheimer's disease in APP/PS1 double transgenic mice.

AKK PROBIO may have a therapeutic effect on gouty arthritis in a gouty arthritis mouse model at a low dosage, and may have a better therapeutic effect at a high dosage.

The above shows that AKK PROBIO of the disclosure has good tolerance, high safety, wide indications and good therapeutic effect, and has very good clinical application prospects.

Preservation Instructions:

Strain number: AKK PROBIO;

Classification and designation: *Akkermansia muciniphila;*

Preservation number: CGMCC No. 20955;

Preservation date: Oct. 26, 2020;

Preservation authority: China General Microbiological Culture Collection; and

Preservation address: No. 3, Courtyard 1, Beichen West Road, Chaoyang District, Beijing.

BRIEF DESCRIPTION OF FIGURES

In the drawings, the name of each group refers to:

Normal=normal group, Control=AOM/DSS-induced colorectal carcinoma model group, Aspirin=aspirin (67 mg/kg) treatment group, AKKP-L=low-concentration Akermann *Mucophilus* treatment group ($10^8$ CFU/kg), AKKP-H=high-concentration *Akkermansia muciniphila* treatment group ($10^9$ CFU/kg), mAKK PRO=inactivated AKK PRO group, Blank=blank control group, and DSS=DSS-induced ulcerative colitis model group (DSS model group).

FIG. 1 shows colony morphology of AKK PROBIO (top) and microscopic examination morphology (bottom)

FIG. 3E shows the photo of colons, and FIG. 3F shows colon length.

FIG. 5 shows an influence of AKK PROBIO on colorectum tissue of colorectal carcinoma mice.

FIG. 6 shows an influence of AKK PROBIO on organs of mice, FIG. 6A shows spleen index, FIG. 6B shows liver index, FIG. 6C shows kidney index. Different letters a to d indicate significant differences according to a Duncan test ($p<0.05$), and NS indicates no significant differences between groups ($p>0.05$).

FIG. 7A shows normal pathological sections of rectum tissue of mice, FIG. 7B shows control pathological sections of rectum tissue of mice, FIG. 7C shows aspirin pathological sections of rectum tissue of mice, FIG. 7D shows AKKP-L pathological sections of rectum tissue of mice, FIG. 7E shows AKKP-H pathological sections of rectum tissue of mice.

FIG. 20 shows detection results of activity of glutamic oxalacetic transaminase (GOT, FIG. 20A shows GOT in liver, FIG. 20B shows GOT in serum) in mice in acute toxicity experiments.

FIG. 21 shows detection results of the content of creatinine (GRE) in mice in acute toxicity experiments.

FIG. 22 shows detection results of the concentration of blood urea nitrogen (BUN) in mice in acute toxicity experiments.

FIG. 23 shows pathological sections of livers (FIG. 23A) and kidneys (FIG. 23B) of mice in acute toxicity experiments.

DETAILED DESCRIPTION

Figure 1A:
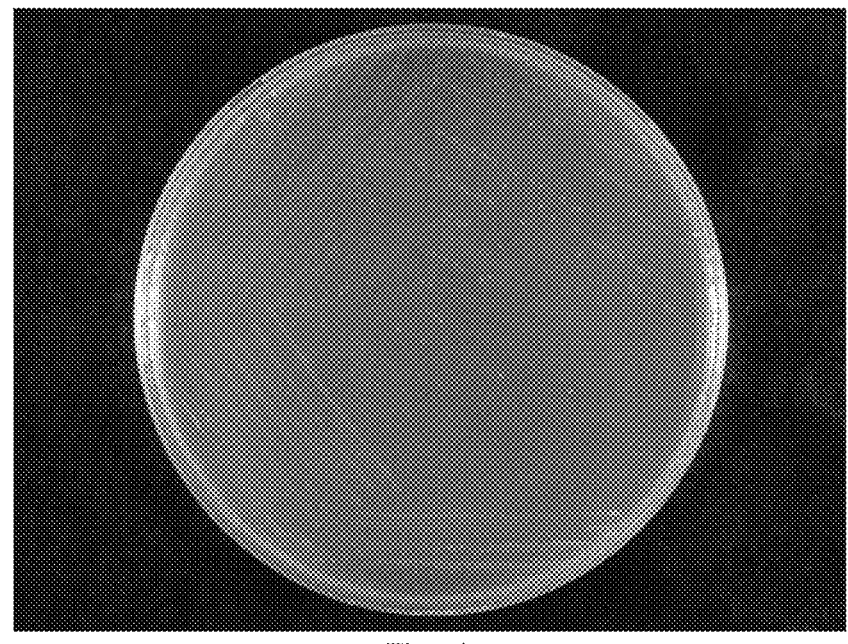
FIG. 1A shows colony morphology of AKK PROBIO.

The disclosure will be further elaborated below in conjunction with specific embodiments. The following embodiments are not used to limit the disclosure, but are only used to illustrate the disclosure. Unless otherwise specified, the experimental methods used in the following embodiments, for which specific conditions are not specified, usually follow the conventional conditions, and the materials and reagents used in the following embodiments are available commercially unless otherwise specified.

Embodiment 1: Strain Isolation

I. Reagent Preparation

A mucin medium was prepared from solution 1 and solution 2, where:

solution 1:1.1 g calcium chloride, 1.0 g magnesium chloride, 5.3 g disodium hydrogen phosphate, 3 g sodium chloride, 4 g dipotassium hydrogen phosphate, 2 g sodium bicarbonate, 2.5 g sodium sulfide, dilute to the volume of 100 mL, and sterilize with high-pressure steam for later use; and solution 2: mucin (Sigma, product number: M1778, CAS number: 84082-64-4) solution.

Preparation of mucin liquid medium: 200 mL of sterile distilled water was taken and placed in a pressurized wide-mouthed bottle; 2 mL of solution 1 and 30 to 40 mL of solution 2 were added into a clean bench; 5 mL of the liquid was drawn with an electric pipette and the drawn liquid was distributed into 15 mL centrifuge tubes; tube caps were loosened and the centrifuge tubes were placed in an anaerobic tank for 3 d, and then, the tube caps were tightened for airtight storage of the drawn liquid at 4° C.

Preparation of mucin solid medium: 20 g/L of agar powder was added into a mucin liquid medium; the mixture $10^{-4}$, $10^{-5}$, and $10^{-6}$, respectively; 500 μL of diluted sample was drawn from a $10^{-2}$ dilution tube; the diluted sample was added into 4.5 mL of mucin liquid medium; $10^{-3}$ to $10^{-6}$ were inoculated into the mucin liquid medium using the same method, with 2 tubes of diluted sample per gradient; and enrichment tubes were placed in an anaerobic constant-temperature incubator and culture was performed at 37° C. for 3 d.

III. Isolation and Culture with Solid Plates

Turbid enrichment tubes were selected; relatively uniform, and suspended enrichment tubes without precipitates, clumps, or filaments were selected from the turbid liquid tubes for isolation and culture with solid plates; $10^{-1}$ to $10^{-6}$ were diluted and the diluted $10^{-1}$ to $10^{-6}$ were applied to the mucin solid medium and a BHI solid medium, with 3 plates of diluted samples per dilution; and the solid plates were placed in a 37° C. anaerobic constant-temperature incubator and culture was performed for 5 d.

IV. Physiological and Biochemical and 16S Identification and Preservation (1) Physiological and biochemical identification of anaerobic bacteria was conducted using a VITEK® 2 ANC identification card (BIOMERIEUX CHINA, product number: 21347). The identification results are as follows:

| Physiological and Biochemical Characteristic VITEK ANC identification card | | | | | | | |
|---|---|---|---|---|---|---|---|
| D-galactose | – | Leucine-arylamidase | – | ELLMAN | – | Phenylalanine-arylamidase |
| L-proline-arylamidase | – | L-pyrrolidone-arylamidase | – | D-cellobiose | – | Tyrosine-arylamidase |
| Alanine-phenylalanine-proline-arylamidase | – | D-glucose | – | D-mannose | – | D-maltose |
| Sucrose | – | Arbutin | – | N-acetyl-D-glucosamine | – | 5-bromo-4-chloro-3-indole-β-D-glucoside |
| Urease | – | 5-bromo-4-chloro-3-indole-β-D-glucuronide | – | β-galactopyranosidase indophenol | – | α-arabinosidase |
| 5-bromo-4-chloro-3-indole-α-D-galactoside | – | β-mannosidase | – | Arginine GP | – | Pyruvate |
| Maltotriose | – | Esculin hydrolysis | – | β-D-fucosidase | – | 5-bromo-4-chloro-3-hydroxyindole-b-N-acetyl-glucosamine |
| 5-bromo-4-chloro-3-indole-α-D-mannoside | – | α-L-fucosidase | – | Phosphatase | – | L-arabinose |
| d-ribose | – | Phenylphosphate | – | α-L-arabinoside | – | D-xylose |

Symbol description: "+" indicates positive; and "–" indicates negative.

was poured into sterile plates at 20 mL per plate; and after cooling and solidification, the plates were placed in a sterile plastic bag for airtight storage at 4° C.

Brain heart infusion (BHI, OXOID, product number: CM1032B) solid medium was poured into a sterile plate, and the sterile plate was placed in a sterile plastic bag for airtight storage at 4° C.

II. Sample Dilution and Enrichment Culture 1 to 2 g of fecal samples were collected from healthy individuals and immediately inoculated into 9 mL of saline, which was denoted as $10^{-1}$; the fecal samples were further diluted for 5 gradients, which were denoted as $10^{-2}$, $10^{-3}$, (2) The cultured solid plates were taken out, and under strong light, milky white, and viscous colonies without miscellaneous bacteria around and with a diameter of less than 1 mm were picked up; the colonies were inoculated into a 9 mL BHI liquid medium with an aseptic operation; the BHI liquid medium was placed in a 37° C. anaerobic constant-temperature incubator and culture was performed for 48 h; and meanwhile, 16S identification was performed.

An identification primer was a conventional primer, a forward primer was 27F (5'→3'): SEQ ID NO. 2, and a reverse primer was 1492R (5'→3'): SEQ ID NO. 3;

Identification PCR system: 1 μL 27F primer solution, 1 μL 1492R primer solution, 12 μL 2×PCR MasterMix, 10 μL sterile water, and 1 μL template; and PCR reaction conditions: 95° C., 5 min; 30 cycles; 95° C., 30 s; 55° C., 30 s; 72° C., 2 min; 72° C., 10 min.

A strain of new bacterium AKK PROBIO of muciniphila was obtained by screening, and its 16S sequence was SEQ ID NO. 1. After NCBI comparison, from the identification result, the new bacterium was classified and designated *Akkermansia muciniphila*. It was deposited on Oct. 26, 2020 in the China General Microbiological Culture Collection Center, with the preservation number of CGMCC No. 20955. The comparison results with some existing strains are as follows:

| Existing strains | Similarity |
| --- | --- |
| *Akkermansia muciniphila* ATCC BAAs-835T (CP001071) | 99.85% |
| *Akkermansia glycaniphila* PytT (KT254068) | 93.71% |
| *Haloferula luteola* YC6886T (FJ032193) | 85.20% |
| *Haloferula harenae* YM23-227T (AB372852) | 85.17% |
| *Persicirhabdus sediminis* YM20-087T (AB331886) | 85.03% |
| *Luteolibacter algae* A5J-41-2 T (AB331893) | 84.87% |
| *Luteolibacter cuticulihirudinis* E100T (JQ429496) | 84.79% |
| *Luteolibacter gellanilyticus* CB-286403T (LN833280) | 84.65% |
| *Luteolibacter pohnpeiensis* A4T-83T (AB331895) | 84.54% |
| *Haloferula sargassicola* MN1-1037T (AB372856) | 84.47% |

Figure 2:
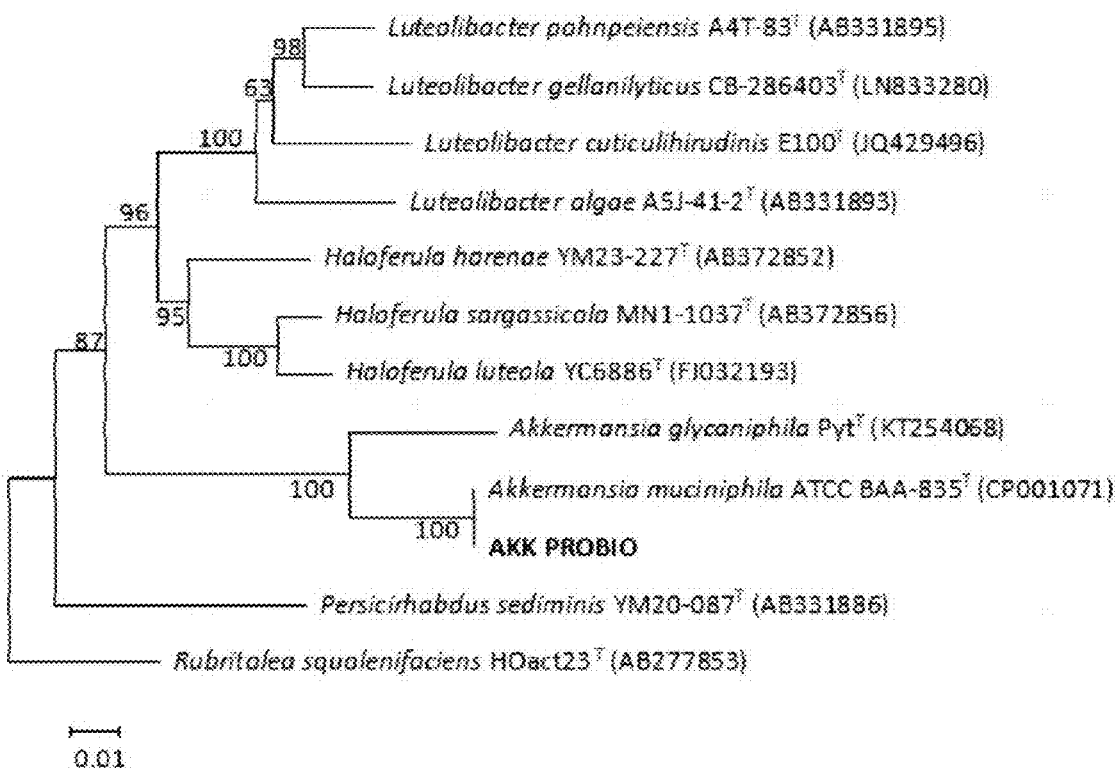
FIG. 2 shows a phylogenetic tree of AKK PROBIO (neighbor joining method, NJ method).

A phylogenetic tree of 16S rDNA sequences of AKK PROBIO and related species is as shown in FIG. 2. The phylogenetic tree of the 16S rDNA sequences of AKK PROBIO and the related species is shown using MEGA software and the neighbor joining method. Calculation of similarity was repeated 1000 times. In the figure, nodes in the phylogenetic tree only show that a bootstrap value is greater than 50%, and the superscript "T" represents a type strain.

Fermented broth was frozen and preserved in a 25% glycerol tube.

Figure 1B:
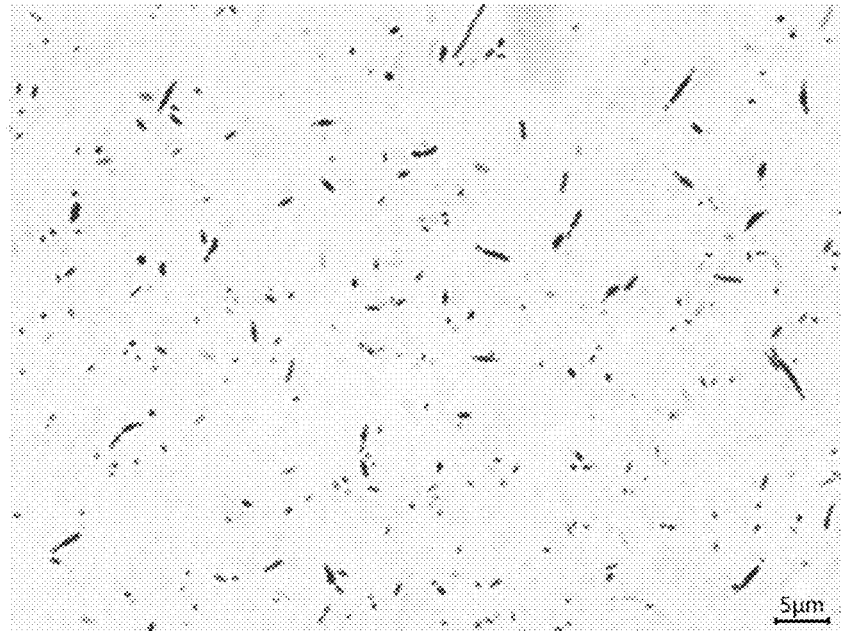
FIG. 1B shows microscopic examination morphology.

AKK PROBIO was subjected to anaerobic culture at 37° C. in a BHI medium for 7 d, and from plate morphology, colonies were light yellow, round, and semi-transparent, and had a moist surface, and neat edges. AKK PROBIO was subjected to anaerobic culture at 37° C. in the BHI medium for 4 d, and a microscopic examination shows that bacterial cells are rod-shaped, with a size ranging from 0.5 to 0.9 μm×0.7 to 3.8 μm, arranged singly or in pairs, and Gram-negative. See FIG. 1.

Embodiment 2: Culture of AKK PROBIO (1) Culture was performed with solid plates, where a medium included the components of BHI+5% sheep blood, and a method for preparing the medium included: weighing a certain volume of required BHI powder according to finished-product requirements; adding agar powder in a proportion of 20 g/L; diluting to a corresponding volume, performing sterilization at 121° C. for 20 min; after sterilization, cooling to 53° C. (not hot to hold) and adding 5% sterile defidrinated sheep blood; and shaking well and pouring 15 to 20 mL into a plate for later use;

where the culture temperature of AKK PROBIO was set to 37° C., and the culture condition was as follows: complete anaerobic culture.

(2) liquid culture (fermented broth culture) was used, where the medium was BHI, the culture temperature was 37° C., and the culture conditions were as follows: 8 layers of gauze, and complete anaerobic culture. Specifically, the liquid culture includes the following steps:

First stage: Taking a 2 mL glycerol tube and inoculate AKK PROBIO with an inoculum size of 10% into a test tube containing 9 mL BHI, and performing anaerobic culture at 37° C. for 24 to 48 h;

second stage: Taking a first-stage fermentation test tube and inoculating AKK PROBIO with an inoculum size of 5% into a triangular flask containing 90 mL BHI, and performing anaerobic culture at 37° C. for 24 h; and third stage: Taking fermented broth from a second-stage triangular flask and inoculating the fermented broth with an inoculum size of 5% into a triangular flask containing 300 mL BHI; performing anaerobic culture at 37° C. for 13 h; and freezing and preserving the culture in a 20% glycerol tube at −80° C.

Embodiment 3: Improvement of Dextran Sulfate Sodium (DSS)-Induced

Ulcerative Colitis in Mice by AKK PROBIO

Animals and their management: male C57BL/6J mice (6 to 10-week-old, weighing 18 to 24 g) purchased from the Beijing Huafukang Biotechnology Co., Ltd, where procedures involving mice were carried out in strict accordance with international animal care standards, and approved by the Animal Protection Institute and Management Committee of Jilin Agricultural University. Adaptive culture was performed for 1 week, and mice were cultured at room temperature (25° C.±1° C.) in a cycle of 12 h of light and 12 h of darkness.

Animal experimental design: 5.0% (wt/vol) DSS (molecular weight: 36,000 to 50,000) was added to drinking water of the mice for 3 consecutive days to induce colitis. Beginning on the first day of taking DSS, the *A. muciniphila* (viable or inactivated, with a concentration of $1 \times 10^{10}$ CFU/mL) was intragastrically administered per day for 9 consecutive days. C57BL/6J mice were randomly divided into four groups: a control group, a DSS model group (DSS), an AKK PRO group, and an inactivated AKK PRO group (mAKK PRO). Physiological indicators of the mice in each group were observed.

Physiological indicators: The physiological indicators are used for assessing health statuses of the mice. The individual scores of the mice were combined to generate disease activity indices (DAI), including changes of body weight, food intake, and fecal consistency. See Table 1 for scoring standards. After the mice were euthanized, the colon length and the liver weight of each mouse in each group were measured, and an immune organ index was calculated according to the following formula: liver index=liver weight (mg)/body weight (g) [Wang, X., et al., Troxerutin Improves Dextran Sulfate Sodium-Induced Ulcerative Colitis in Mice. J Agric Food Chem, 2021. 69 (9): p. 2729-2744.].

TABLE 1

| Disease Activity Index (DAI) Scoring Scale | | |
|---|---|---|
| Indicators | Degree | Score |
| Body weight | 0-1 g | 0 |
|  | 1-1.5 g | 1 |
|  | 1.5-2 g | 2 |
|  | 2-2.5 g | 3 |
|  | >2.5 g | 4 |
| Food intake | 0-0.5 g | 0 |
|  | 0.5-1 g | 1 |
|  | 1-1.5 g | 2 |
|  | 11.5-2 g | 3 |
|  | >2 g | 4 |
| Fecal morphology | Normal morphology | 0 |
|  | Loose stools | 1 |
|  | Watery diarrhea | 2 |
|  | Watery diarrhea with little blood | 3 |
|  | Watery diarrhea with severe bleeding | 4 |

Statistical Analysis:

Statistical analysis was performed on data using Graph-Pad, and all data was expressed as mean±standard deviation (SD). t test was used for statistical significance between two groups, and two-way analysis of variance (ANOVA) was used for comparison between two groups, and $P < 0.05$ indicated that the difference was significant.

Result Analysis (1) Ingestion of the *A. muciniphila* can Significantly Reduce Physiological Injury in DSS-Induced Colitis Mice In order to determine whether the *A. muciniphila* had an improvement effect on colitis, acute colitis was induced with or without the *A. muciniphila* using 5.0% DSS.

Figure 3A:
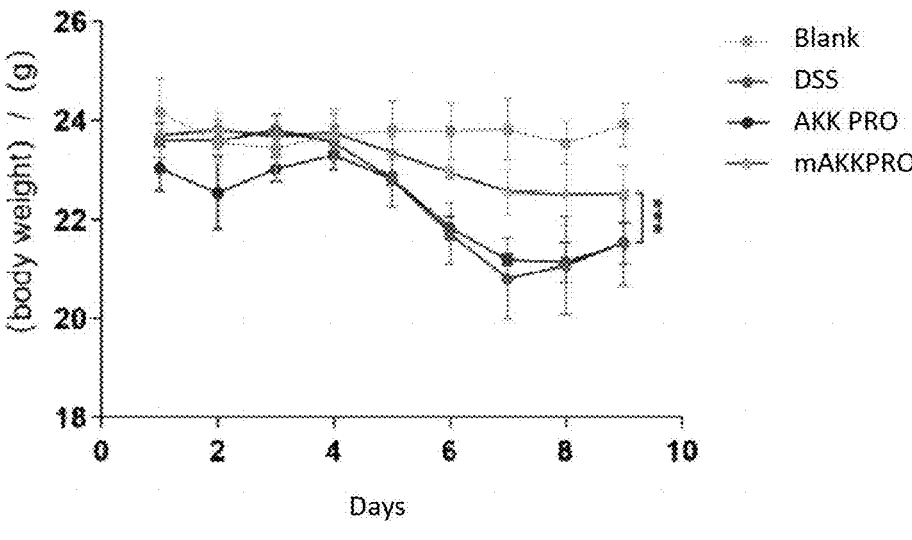
FIG. 3A shows body weight.
Figure 3B:
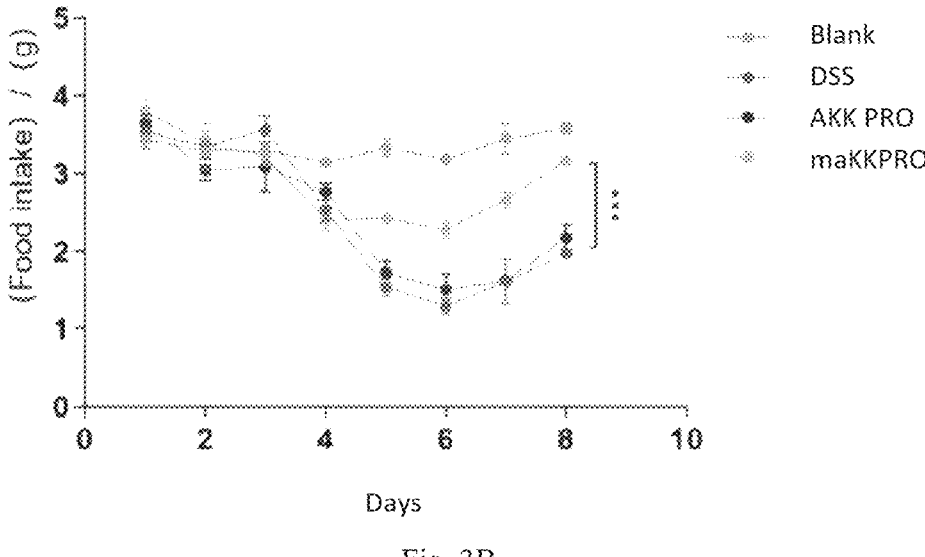
FIG. 3B shows food intake.
Figure 3C:
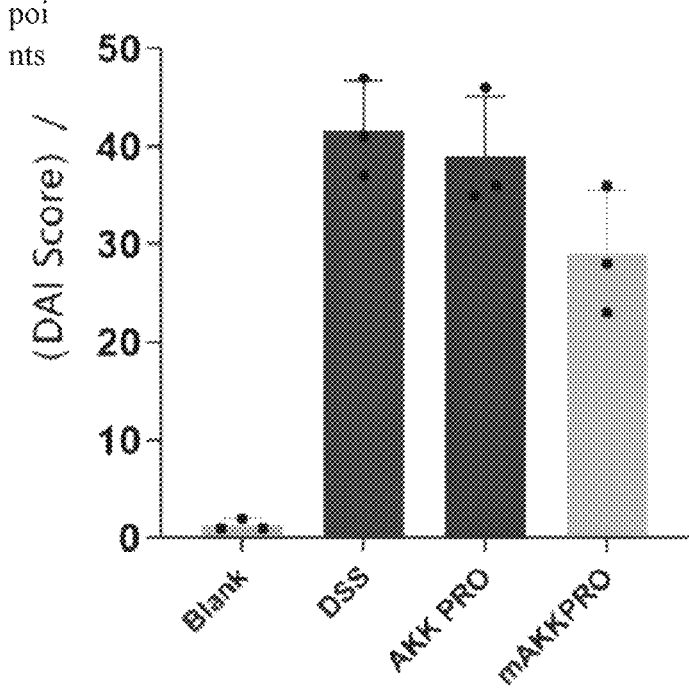
FIG. 3C shows DAI score.
Figure 3D:
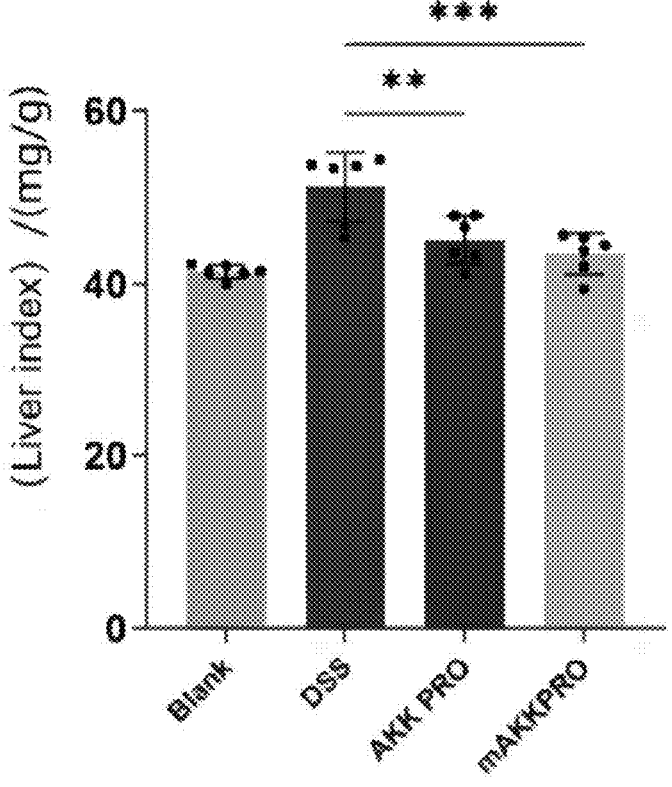
FIG. 3D shows liver index.
Figure 3:
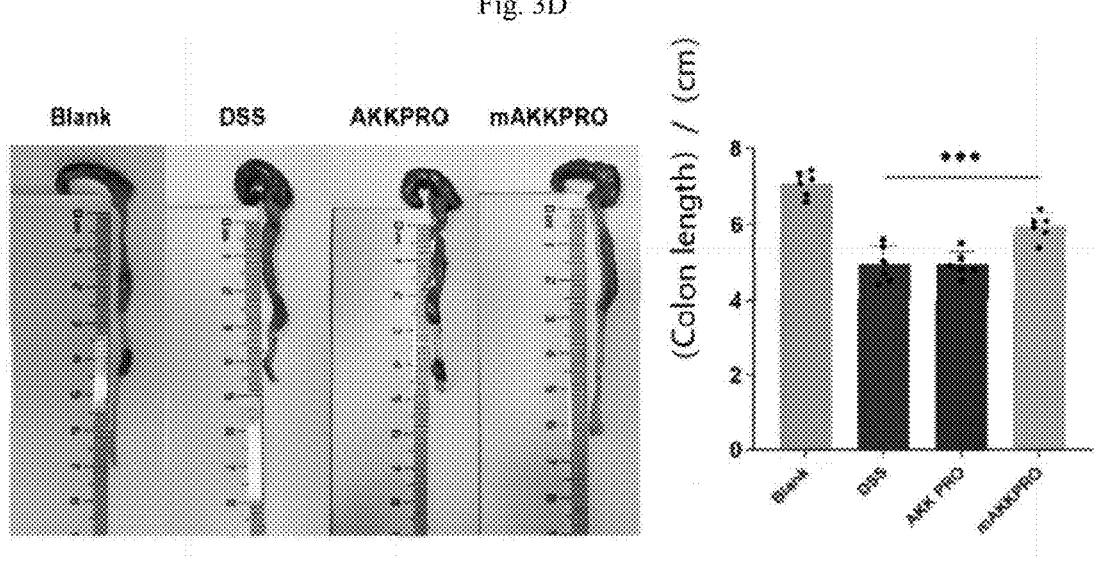
FIG. 3 shows an influence of AKK PROBIO on physiological indicators in DSS-induced ulcerative colitis mice.

As can be seen from FIG. 3:

mice treated with both DSS and the *A. muciniphila* had less body weight (a) and food intake (b) reduced and a lower DAI score (c) than the mice in the model group.

Meanwhile, an increase in an immune organ index and a decrease in colon length indicated an increase in inflammation. The results show that the immune organ index (d) of the DSS group is significantly increased ($P < 0.05$), but is significantly decreased after treatment with the *A. muciniphila*.

The colon length (e) of the mice in the DSS group was significantly reduced ($P < 0.05$), but was significantly increased ($P < 0.05$) after ingestion of the *A. muciniphila*.

The above results indicate that the *A. muciniphila* can significantly improve the physiological injury in the colitis mice.

Embodiment 4: Effect of AKK PROBIO Intervention on AOM/DSS-Induced Colorectal Carcinoma Mice Some of experimental reagents used in this embodiment are sourced from:

Azoxymethane (AOM), Sigma-Aldrich; dextran sulfate sodium (DSS), MP Biomedicals; enteric-coated aspirin, Bayer Healthcare Co., Ltd.; ELISA kit for interleukin-1β (IL-1β), interleukin-6 (IL-6), interferon-γ (IFN-γ), inducible NO synthase (iNOS), nuclear factor κB (NF-κB), Shanghai Enzyme-linked Biotechnology Co., Ltd.; RNase-Free water, Beijing Solarbio Science & Technology Co., Ltd.; qPCR SYBR Green Master Mix, Shanghai Yeasen Biotech Co., Ltd.; total RNA extraction kit (TRIzol™ Reagent), and reverse transcription kit (Revert Aid First Strand cDNA Synthesis Kit), Thermo Fisher Scientific. All other reagents are domestic biochemical reagents or analytically pure.

Some of instruments and devices used in this embodiment are as follows:

6D45415 Upright Microscope, Olympus Corporation, Japan; Bioprep-24 Biological Sample Homogenizer and Nano-300 micro-spectrophotometer, Hangzhou Allsheng Instruments Co., Ltd.; A200 Gradient PCR System, Hangzhou LongGene Scientific Instruments Co., Ltd.; and VLBLOTD1 Multimode Reader, StepOnePlus™ Real-Time PCR System, Thermo Fisher Scientific (Suzhou) Co., Ltd.

Experimental Animals and Grouping Treatment:

6-week-old SPF male C57BL/6 mice, purchased from the Chongqing Lepitt Biotechnology Co., Ltd. The mice were raised in a standardized laboratory with room temperature of 25° C.±2° C., relative humidity of 50%±5%, and 12 h of light/12 h of darkness. The animals were randomly divided into 5 groups after 1 week of adaptive feeding: a normal group, a model group, an aspirin positive control group, an AKK PROBIO low-concentration (AKKPL) group, and an AKK PROBIO high-concentration (AKKPH) group. In experiments, mice were given free feeding and water. On the first day of experimental molding, the mice in the model group, the aspirin group, and the AKKP group were injected intraperitoneally with AOM at a dosage of 10 mg/kg, and were fed with 2.5% DSS aqueous solution at weeks 2, 5, and 8. The mice in the normal group and model group were intragastrically administrated with sterile saline; the mice in the aspirin group were intragastrically administrated with an aspirin solution at 67 mg/kg, and the mice in the AKKPL group and the AKKPH group were intragastrically administrated at dosages of $1 \times 10^8$ CFU/kg and $1 \times 10^9$ CFU/kg, respectively, for 10 consecutive weeks. In the experiments, diet, activity, vigor and hair conditions, and fecal properties of the mice in each group were observed. Each mouse was weighed per week and the body weights were recorded. After the experiments, blood was collected from eyeballs and the mice were sacrificed by removing their vertebrae. The mice were dissected to take out large intestine tissue, spleen tissue, liver tissue, and the kidney tissue for later testing.

(1) Determination of Organ Indices

After the mice were dissected, the large intestine tissue, the spleen tissue, the liver tissue, and the kidney tissue were taken out and weighed. An organ Index was calculated using a formula, while the colorectum length of the mouse was measured and the colorectal tumorigenesis number of the mouse was recorded. Organ index=organ weight (mg)/mouse body weight (g).

(2) Pathological Observation of Rectum Tissue

After being fixed in a tissue fixative for 24 h, the rectum of the mouse was transferred into 95% ethanol for dehydration, and then the dehydrated rectum was placed in xylene to replace alcohol in the tissue to make the rectum tissue transparent. Then, the treated rectum was embedded with paraffin. The embedded rectum was sectioned by a microtome, and then a tissue section was stained with H&E and fixed, obtaining a pathologic tissue section, with a thickness of 2 to 3 μm, of the rectum of the mouse, and the pathologic tissue section was observed under the upright microscope.

(3) Determination of Levels of Inflammation-Related Factors in Serum of Mouse

Whole blood was collected from the eyeballs, and centrifuged at 4000 r/min and 4° C. for 10 min to separate supernatant serum. According to the instruction of the ELISA kit, the levels of IL-1β, IL-6, IFN-γ, iNOS and NF-κB in the serum of the mouse were determined.

(4) Determination of Expressions of Inflammation and Apoptosis-Related Genes in Colon Tissue of Mice About 50 mg colon tissue was taken and cleaned with saline, and the cleaned colon tissue was placed in a homogenization tube containing 6 zirconia beads, and 500 μL TRIzol™ reagent was added to extract RNA in the tissue. The purity and concentration of RNA were determined using the micro-spectrophotometer. As an indicator value for nucleic acid testing, A260/A280 has a ratio between 1.8 and 2.0, indicating that the RNA purity is relatively high, and follow-on experiments can be conducted. Then, after cDNA was generated by reverse transcription, a reaction system containing 1 μL cDNA was prepared. Other reagents include 10 μL qPCR SYBR Green Master Mix, 7 L sterile distilled water, 1 μL forward primer and 1 μL reverse primer. qRT-PCR amplification reaction conditions: 95° C., 10 s, 60° C., 30 s, 40 cycles; 95° C., 15 s, 60° C., 60 s, 95° C., 15 s. Taking Eef2 as an internal reference gene, the mRNA relative expression of each target gene was calculated according to formula $2^{-\Delta\Delta Ct}$. Table 2 shows primer sequences used in this experiment.

TABLE 2

| | Primer Sequences | | |
| --- | --- | --- | --- |
| Genes | Genebank number GenBank accession numbers | Primer Sequence (5'-3') | Product size (bp) |
| Eef2 | NM_007907.2 | F: SEQ ID NO.4 R: SEQ ID NO.5 | 123 |
| p50 | NM_008689.3 | F: SEQ ID NO.6 R: SEQ ID NO.7 | 96 |
| p52 | NM_001177370.1 | F: SEQ ID NO.8 R: SEQ ID NO.9 | 212 |
| p65 | NM_009045.4 | F: SEQ ID NO.10 R: SEQ ID NO.11 | 126 |
| IKKβ | NM_010546.2 | F: SEQ ID NO.12 R: SEQ ID NO.13 | 228 |
| Caspase-9 | NM_015733.5 | F: SEQ ID NO.14 R: SEQ ID NO.15 | 109 |
| Bid | NM_007544.4 | F: SEQ ID NO.16 R: SEQ ID NO.17 | 107 |
| Bim | NM_207680.2 | F: SEQ ID NO.18 R: SEQ ID NO.19 | 96 |

(5) Data Analysis

All results in the experiment are expressed as mean±standard deviation, and a one-way ANOVA method in IBM SPSS27.0 software was used to test whether there was a significant difference between the experimental results of each group at the $P < 0.05$ level.

Figure 4:
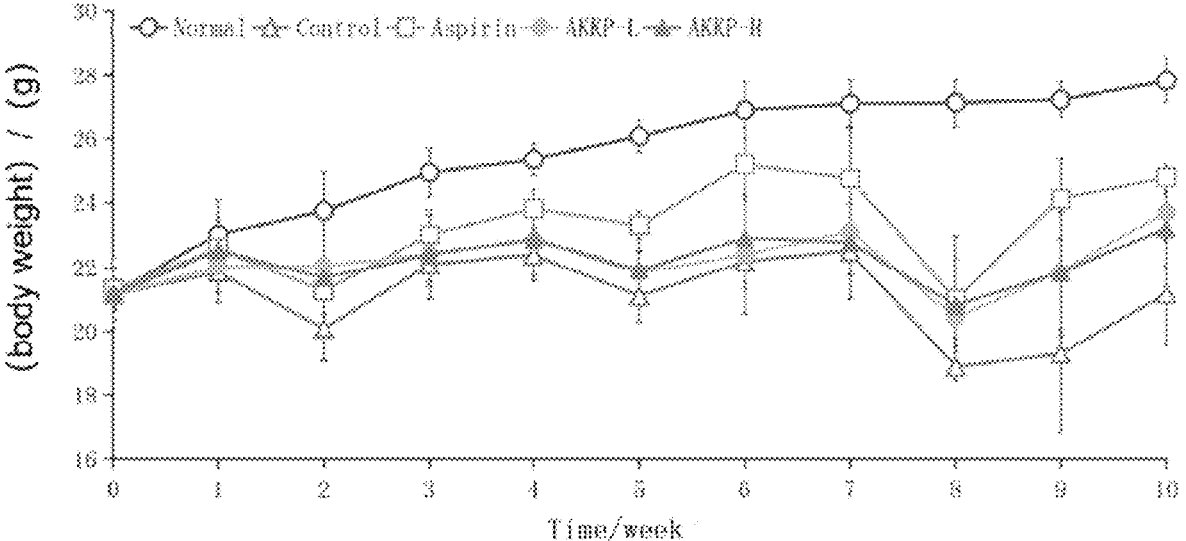
FIG. 4 shows an influence of AKK PROBIO on the body weight of colorectal carcinoma mice.

(6) Experimental Results 6.1. Influence of AKK PROBIO on Body Weight of Colorectal Carcinoma Model Mice:

The mice in the normal group were healthy, moved freely, had dark and shiny coats, ate and drank water normally, and had no diarrhea and bloody stools, while the mice in the remaining 4 groups had loose stools, rectal prolapse, bloody stools, and body weight loss. As shown in FIG. 4, which is a statistical chart showing changes of body weight of mice in each group. During the administration of DSS at a concentration of 2.5%, the body weight of modeled mice in each group shows a declining trend, and after the administration was stopped, the body weight of the mice in each group shows a gradually increasing trend. At the end of the experiment, the body weight of the modeled mice in each group was significantly lower than that of the mice in the normal group, where the mice in the model group had the least body weight loss, while the mice in the aspirin group and the AKKP intervention group rose again in body weight.

Compared with that of the mice in the normal group, the body weight of the mice in the remaining four groups at the end of the experiment showed significant differences ($P < 0.05$). The results indicate that AOM/DSS can cause the body weight loss in the mice, and aspirin and AKKP intervention can alleviate the body weight loss in the mice to a certain extent.

Figure 5A:
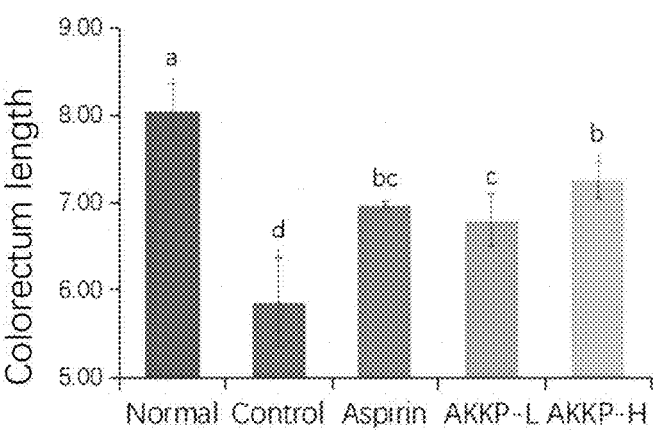
FIG. 5A shows colorectum length.
Figure 5B:
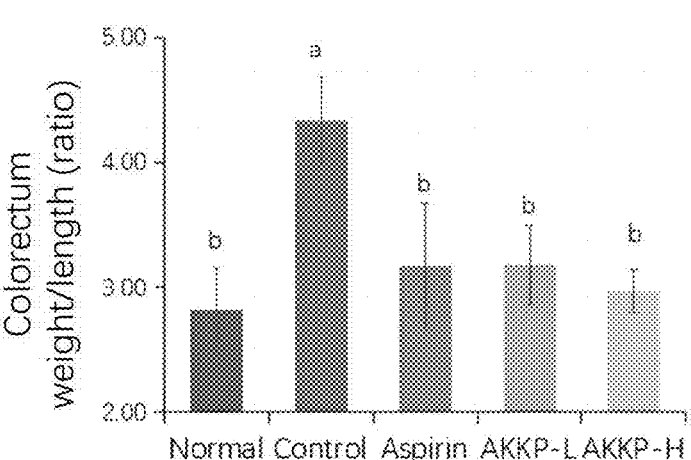
FIG. 5B shows colorectum weight/length (ratio)
Figure 5C:
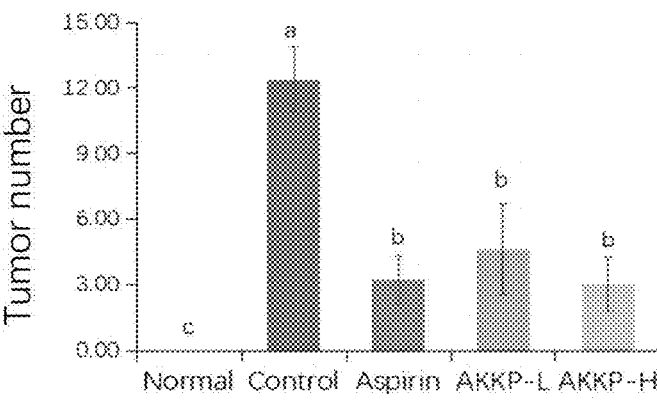
FIG. 5C shows tumor number. Different letters a to d indicate significant differences according to Duncan test ($p<0.05$).

6.2. Influence of AKK PROBIO on Colorectums of Colorectal Carcinoma Model Mice:

As shown in FIG. 5, which shows changes of the colorectum of the mouse in each group. When colorectal inflammation occurs in the mouse, the colorectum in the mouse is shortened to a certain extent, and the colorectal inflammation can be analyzed from the length of the colorectum. Compared with that in the normal group, the colorectums in the remaining four groups are relatively short ($P < 0.05$). Compared with that in the model group, the colorectum in the Aspirin group was relatively long as well as in the AKKP group ($P < 0.05$). As can be seen from the above, AKKP intervention can alleviate shortening of the colorectum of the mouse.

The colorectum weight/length (ratio) of the mouse in the normal group was 2.81±0.34, the ratio in the model group was 4.34±0.35, the ratio in the aspirin group was 3.17±0.50, the ratios in the AKKPL group and the AKKPH group were 3.18±0.31 and 2.97±0.18, respectively. The model group showed significant differences compared to the normal group, the aspirin group, and the AKKP group ($P < 0.05$). This indicates that AKKP intervention can reduce the mouse colorectum weight/length (ratio).

Compared with that in the normal group, the colorectal tumorigenesis number in the remaining four groups was significantly larger ($P < 0.05$). Compared with that in the model group, the colorectal tumorigenesis number in the aspirin group was significantly smaller as well as in the AKKP group ($P < 0.05$). The results indicate that AKKP intervention can effectively reduce the number of intestinal tumors in the mice.

6.3. Influence of AKK PROBIO on Spleen, Liver, and Kidney Indices in Colorectal Carcinoma Model Mice:

The organ index is one of the basic indices in biomedical research and an important basis for research. As shown in FIG. 6, which is a statistical chart showing spleen and liver indices of mice in each group. Compared with those in the normal group, the spleen weight and liver weight of the mouse in the model group were significantly increased ($P < 0.05$), and differences were statistically significant. Compared with those in the model group, the spleen weight and the liver weight in the aspirin group were both reduced as well as in the AKKP group, and differences were statistically significant ($P < 0.05$). The renal tissue of the mice in the five groups remained structurally normal, and there was no significant difference between the groups ($P > 0.05$). It can be seen that AKKP can effectively alleviate the rise in spleen and liver indices of colorectal carcinoma caused by AOM/DSS.

Figure 7:
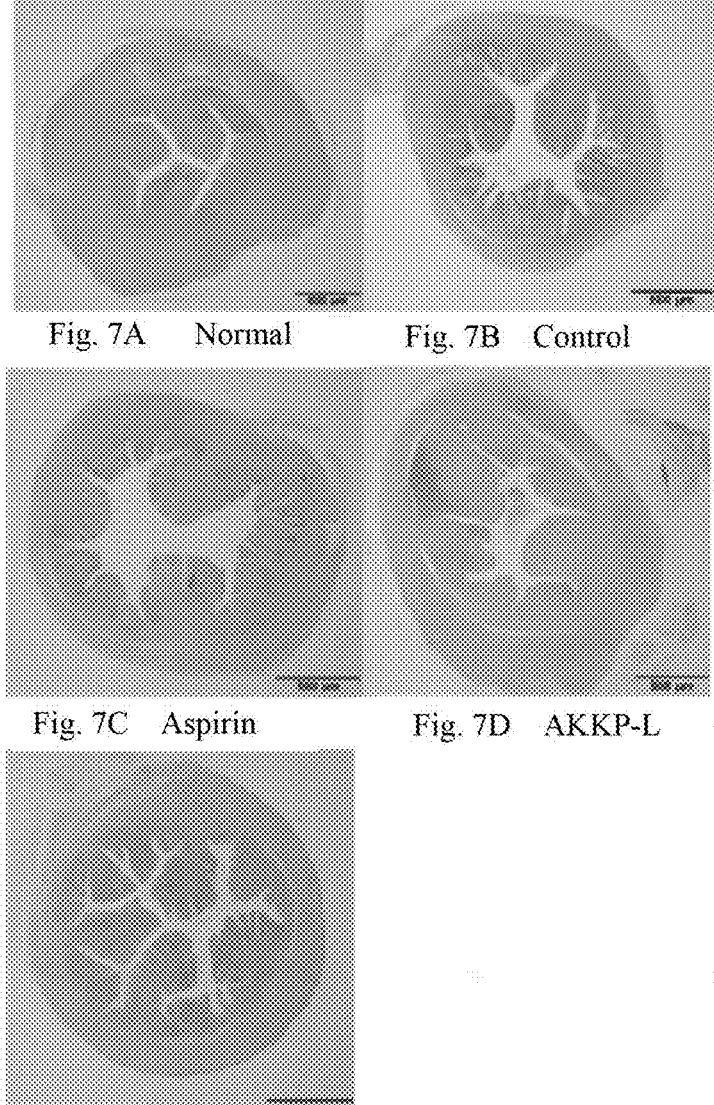
FIG. 7 shows pathological sections of rectum tissue of mice.

6.4. Influence of AKK PROBIO on Pathological Morphology of Rectum Tissue in Colorectal Carcinoma Model Mice:

As shown in FIG. 7, the mice in the normal group had intact mucosal epithelial cells of rectum tissue, normal crypts, glands arranged neatly, and no ulcers. From the model group, it was observed that the rectal mucosa was severely eroded, almost all crypts were destroyed, goblet cells sharply decrease, inflammatory cell infiltration occurs, glands were disordered, and ulcers are severe. The mice in the aspirin group, the AKKPL group and the AKKPH group had no obvious erosion found in the rectal mucosa, relatively intact crypts, glands arranged neatly, and relatively intact goblet cells. The histological results indicate that AKKP effectively reduces AOM/DSS-induced pathological injury to the rectum tissue of the mice.

Figures 8, 8A, 8B, 8C, 8D, 8E:
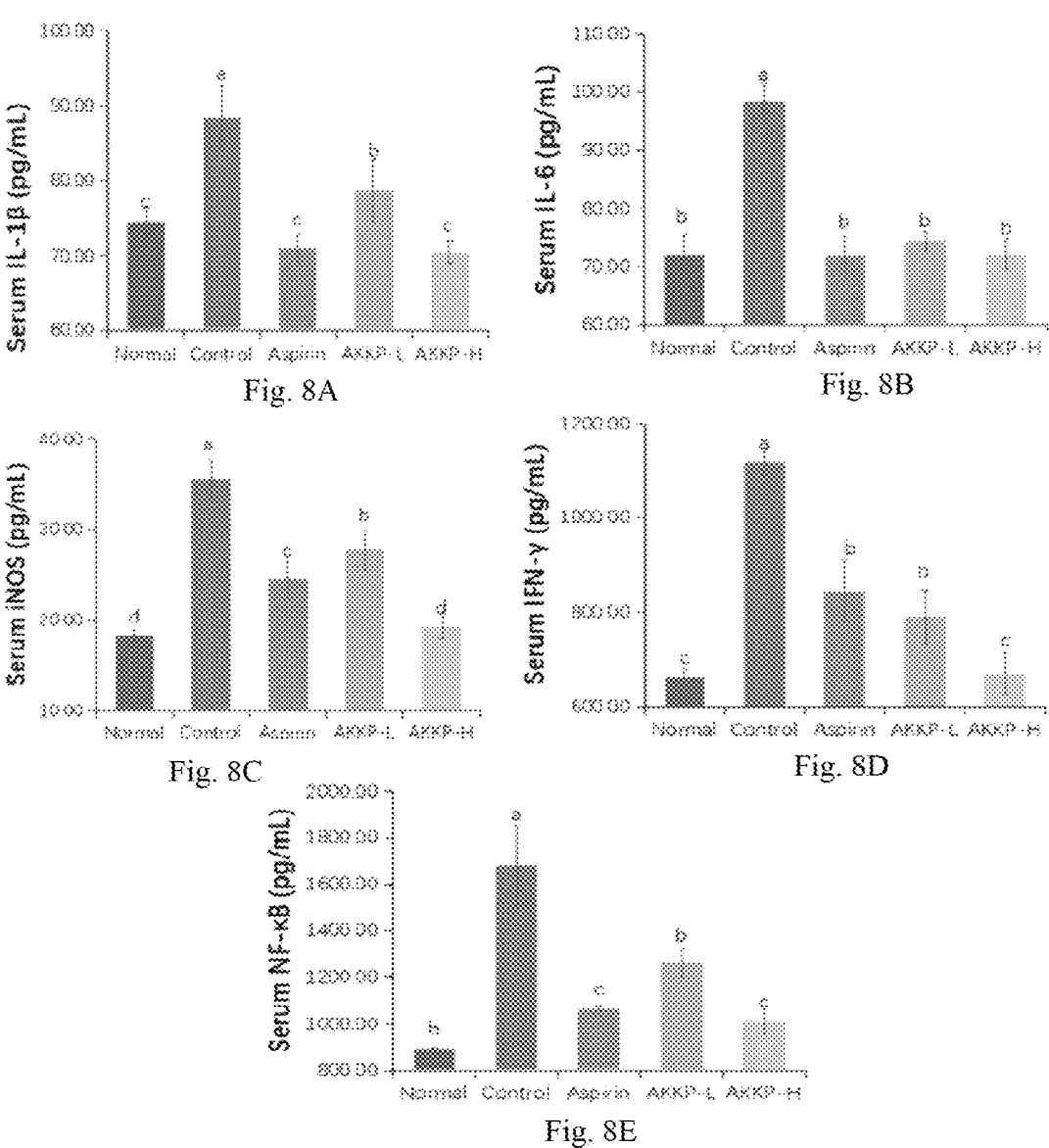
FIG. 8 shows levels of the cytokines, in the serum of the mouse.
FIG. 8A shows IL-1β.
FIG. 8B shows IL-6.
FIG. 8C shows IFN-γ.
FIG. 8D shows iNOS.
FIG. 8E shows NF-κB. Different letters a to d indicate significant differences according to Duncan test ($P<0.05$).

6.5. Influence of AKK PROBIO on Levels of Serum Inflammatory Factors in Colorectal Carcinoma Model Mice:

Cytokines are a type of small molecule proteins synthesized by immune cells and certain non-immune cells, and can bind to corresponding receptors to regulate immune responses [Minxuan X, Sun Y, Dai X, et al. Fisetin attenuates high fat diet-triggered hepatic lipid accumulation: A mechanism involving liver inflammation overload associated TACE/TNF-α pathway [J]. Journal of Functional Foods, 2019, 53, 7-21.], mediate inflammation and involved in tissue repair [Bamias G, Arseneau K O, Cominelli F. Cytokines and Mucosal Immunity. Curr. Opin [J]. Gastroenterol, 2014, 30, 547-552.]. Neutrophil infiltration of colonic mucosae and macrophages secretes a large number of pro-inflammatory cytokines, and inhibits the secretion of anti-inflammatory cytokines during inflammation, thereby exacerbating the inflammatory state [Shukla P K, Chaudhry K K, Mir H, et al. Chronic Ethanol Feeding Promotes Azoxymethane and Dextran Sulfate Sodium-Induced Colonic Tumorigenesis Potentially by Enhancing Mucosal Inflammation [J]. BMC Cancer 16, 2016.]. As shown in FIG. 8, which shows determination results of levels of the related pro-inflammatory cytokines IL-1β, IL-6, IFN-γ, iNOS and NF-κB.

As a pro-inflammatory factor, IL-1β can promote activation and aggregation of inflammatory cells, increase permeability of epithelial and endothelial cells, exacerbate inflammation of intestinal mucosa, and mediate hyperpathia in inflammation [Park J S, Choi J, Hwang S H, et al. Cottonseed Oil Protects against Intestinal Inflammation in Dextran Sodium Sulfate-Induced Inflammatory Bowel Disease [J]. Med. Food 2019, 22, 672-679.]. The content of IL-1β in the serum of the mouse in the model group was maximum, and the content of IL-1β in the serum of the mouse in the normal group was lower than that in the model group as well as in the aspirin group and in the AKKP group, and there was a significant difference (P<0.05). This indicates that AKKP can significantly reduce the level of IL-1β in the serum of CRC mice.

IL-6 is a pleiotropic inflammatory regulatory factor. As the most representative member of the interleukin family, it is a factor transmitting cellular signals that was first found in white blood cells. It is involved in inflammatory responses and immune regulation to mediate carcinogenesis. [Zeng Xinyu, Study on Influence of *Bifidobacterium* Preparations on Postoperative Recovery of Elderly Patients with Colorectal Carcinoma under ERAS Pathway [D]. Hunan Normal University, 2021.]. Compared with that in the normal group, the content of IL-6 in the serum of the mouse in the model group was maximum, and there was a significant difference therebetween (P<0.05). The content of IL-6 in the serum of the mouse in the aspirin group was reduced as well as in the AKKP group, but there was no significant difference therebetween (P>0.05). This indicates that AKKP can significantly reduce the inflammatory factors in the serum of the CRC mice.

INF-γ is a disaccharide protein, which can seriously influence the structure and function of intestinal epithelial cells, and increase the permeability of intestinal mucosa [Zingoni A, Sornasse T, Cocks B G, et al. Cross-talk between activated human NK cells and CD4 T cells via OX40-OX40 ligand interactions. [J]. Immunol, 2004, 173: 3716-3724.]. Research has shown that the level of IFN-γ increases in intestinal inflammation, thereby exerting an immune regulatory effect [Ferrier L, Mazelin L, Cenac N, et al. Stress-induced disruption of colonic epithelial barrier: role of interferon-gamma and myosin light chain kinase in mice [J]. Gastroenterology 125 795-804. 2003]. Compared with that in the normal group, the content of IFN-γ in the serum of the mouse in the model group was maximum, and there was a significant difference therebetween (P<0.05). Compared with that in the model group, the content of IFN-γ in the serum of mice in the aspirin group was reduced as well as in the AKKP group (P<0.05). The content in the AKKPH group was similar to that in the normal group, and there was no significant difference therebetween (P>0.05).

iNOS is a messenger molecule, which can produce nitric oxide (NO). When DSS causes inflammation in the body, high NO expression will exacerbate inflammation and promotes high expression of iNOS [Pan Y, Ning Y, Hu J, et al. The Preventive Effect of *Lactobacillus plantarum* ZS62 on DSS-Induced IBD by Regulating Oxidative Stress and the Immune Response [J]. Oxid Med Cell Longev2021.]. The content of iNOS in the serum of the mouse in the model group was maximum. Compared with that in the model group, the content of iNOS in the serum of the mouse in the normal group was reduced as well as in the aspirin group and in the AKKP group, and there were significant differences between the three groups (the normal group, the aspirin group and the AKKP group) and the model group (P<0.05).

As one of the indicators of the occurrence and development of colorectal carcinoma, NF-κB is involved in the response of cells to stimuli. Its level is abnormally elevated, which is related to various factors such as inflammation, cancer, autoimmune diseases, and can reflect the condition of a CRC patient. [Shi Xinpeng, Luo Xiaoyong, Li Chaoping, et al. Influence of Cetuximab Combined with Chemotherapy on Short-Term Therapeutic Effectiveness on Patients with Drug-Resistant Advanced Colorectal Carcinoma and Levels of NF-κB, EGFR, and HER-2 in Serum [J]. Practical Clinical Journal of Integrated Traditional Chinese and Western Medicine, 202121 (19): 92-93.]. The content of NF-κB in the serum of the mouse in the model group was maximum. Compared with that in the model group, the content of NF-κB in the serum of the mouse in the normal group was reduced as well as in the aspirin group and in the AKKP group (P<0.05). The content in the AKKPH group was similar to that in the aspirin group, and there was no significant difference therebetween (P>0.05).

6.6. Influence of AKK PROBIO on mRNA Expressions of Related Factors in Colon Tissue of Colorectal Carcinoma Model Mice:

1) mRNA Expressions of Inflammatory Pathway-Related Factors in Colon Tissue

NF-κB is composed of five transcription factors. These transcription factors regulate the expression of various genes involved in various biological processes. These processes include inflammation, cell development and differentiation, cell cycle progression, cell migration and the like [Wei H, Prabhu L, Hartley A V, et al. Gene Expression and Regulation in Mammalian Cells-Transcription from General Aspects. IntechOpen; London, UK: 2018. Methylation of NF-κB and its Role in Gene Regulation p. 291.]. The NF-κB family includes the following members: RelA/p65, RelB, c-Rel, NF-κB1 (p50/p105) and NF-κB2 (p52/p100). Research has shown that under the induction of AOM/DSS, an NF-κB signaling pathway of the mouse was activated, which was manifested as an increase in inflammation level in the body. Therefore, the mice can be protected from inflammatory stimuli and the occurrence and development of CRC are intervened by suppressing NF-κB signaling pathway.

Figures 9, 9A, 9B, 9C, 9D:
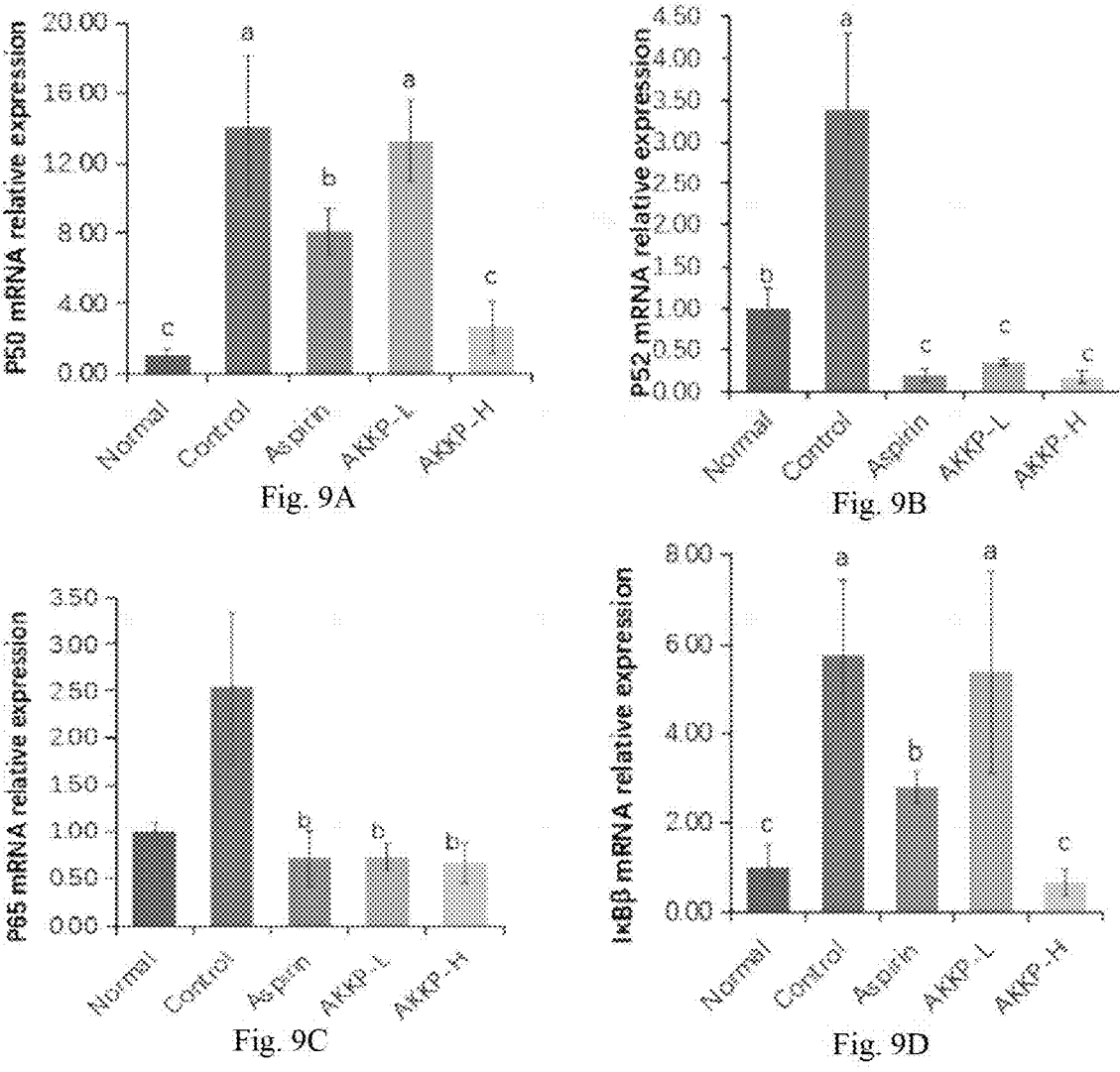
FIG. 9 shows mRNA relative expressions of inflammatory pathway-related genes in colon tissue of mice.
FIG. 9A shows p50.
FIG. 9B shows p52.
FIG. 9C shows p65.
FIG. 9D shows IκBβ. Different letters a to c indicate significant differences according to Duncan test ($P<0.05$).

FIG. 9 shows mRNA expressions of p50, p52, p65, and IκBβ.

The mRNA expressions of p50 and IκBβ in the colon tissue of the mouse in the model group were maximum, the mRNA relative expressions of p50 and IκBβ in the colon tissue of the mouse in the aspirin group were significantly reduced as well as in the AKKPH group (P<0.05), and there was no significant difference between the high-concentration group and the normal group in relative expressions of p50 and IκBβ in the colon tissue of the mice (P>0.05).

The mRNA expressions of p52 and p65 in the colon tissue of the mouse in the model group were maximum, the mRNA relative expressions of p52 and p65 in the colon tissue of the mouse in the normal group were significantly reduced as well as in the aspirin group and the AKKP group (P<0.05), and there was no significant difference between the AKKPH group and the aspirin group in relative expressions of p52 and p65 in the colon tissue of the mice (P>0.05).

2) mRNA Expressions of Apoptosis Pathway-Related Factors in Colon Tissue

The mechanism of apoptosis is very complex and involves many signaling pathways. Apoptosis can be triggered in cells via caspase-mediated extrinsic or intrinsic pathways, which is mainly executed by a family of proteases called caspases (cysteine, aspartate specific proteases) [Li J, Yuan J. Caspases in apoptosis and beyond. Oncogene. 2008; 27:6194-6206.]. The caspases are the core of the mechanism of apoptosis, as they are both initiators (caspase-2, caspase-8, caspase-9 and caspase-10, mainly responsible for initiation of apoptosis pathways) of cell death and executors (caspase-3, caspase-6 and caspase-7, responsible for clear cleavage of cellular components) [Thornberry N A, Laxebnik Y. Caspases: enemies within. Science. 1998; 281: 1312-1316.]. The intrinsic pathway is closely regulated by a B-cell lymphoma 2 (Bcl-2) family of intracellular proteins. Bid is a pro-apoptotic member of the Bcl-2 family, and was found in CRC cells and is directly regulated by miR-20a, thereby inducing apoptosis of mitochondrial cells [Huang G, Chen X, Cai Y, Wang X, Xing C. miR-20a-directed regulation of BID is associated with the TRAIL sensitivity in colorectal cancer. Oncol. Rep. 2017; 37:571-578.]. Bim mediated intrinsic apoptosis regulates the apoptosis of the CRC cells [Drury L J, Wendt M K, Dwinell M B. CXCL12 chemokine expression and secretion regulates colorectal carcinoma cell anoikis through Bim-mediated intrinsic apoptosis. PLoS One. 2010; 5: e12895.].

Figures 10, 10A, 10B, 10C:
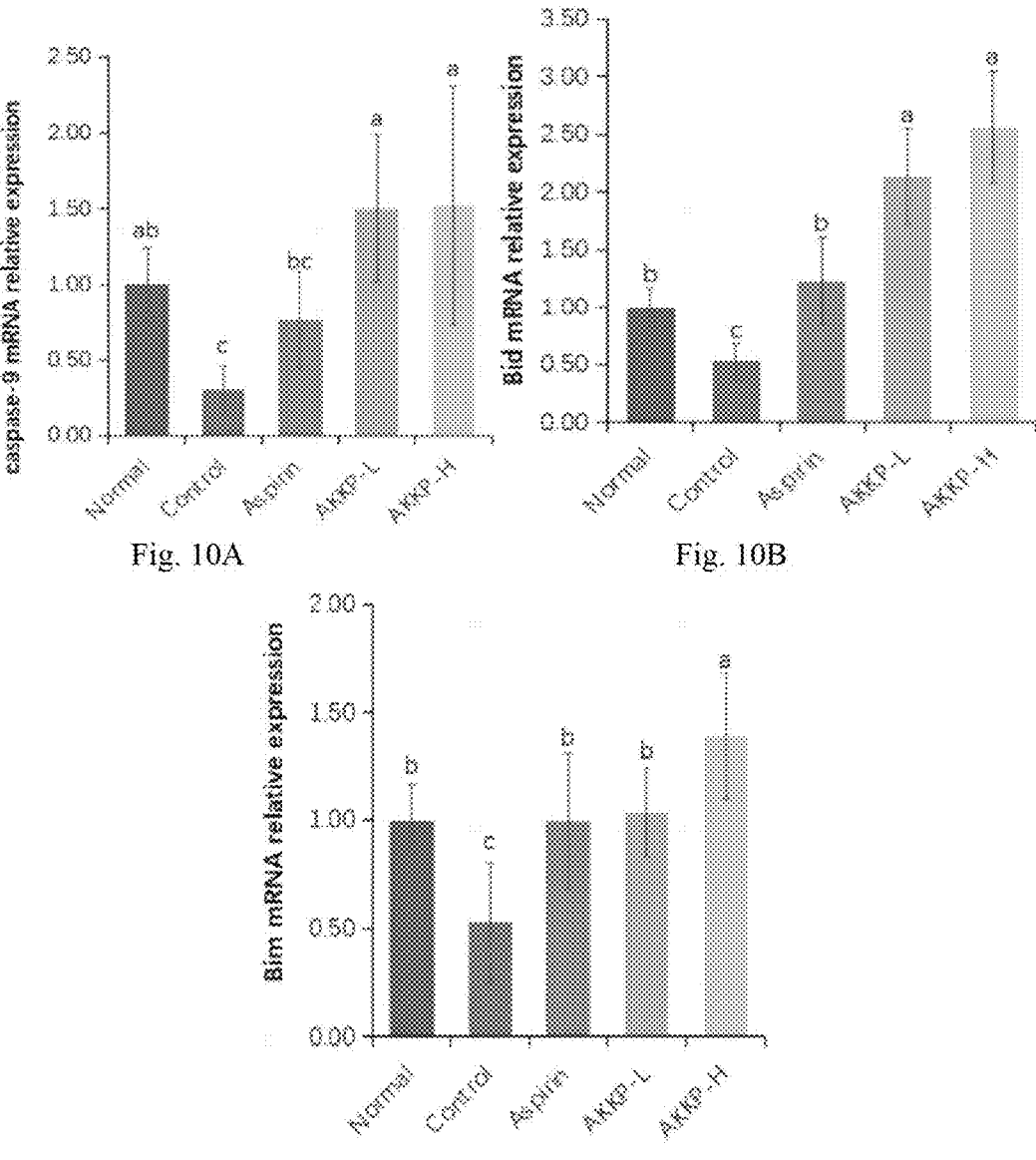
FIG. 10 shows mRNA relative expressions of apoptosis pathway-related genes in colon tissue of mice.
FIG. 10A shows caspase-9.
FIG. 10B shows Bid.
FIG. 10C shows Bim. Different letters a to c indicate significant differences according to Duncan test ($P<0.05$).

FIG. 10 shows mRNA expressions of caspase-9, Bid, and Bim. The mRNA relative expressions of caspase-9, Bid, and Bim in the colon of the mouse in the model group were minimum, while the mRNA relative expressions of caspase-9, Bid, and Bim in the colon tissue of the mouse in the normal group were significantly increased as well as in the aspirin group and in the AKKP group (P<0.05), and the mRNA expressions in the AKKP group showed a concentration dependent trend. With the increase of the intragastric administration concentration of AKKP, the mRNA expressions of caspase-9, Bid, and Bim in the colon of the mouse in the AKKPH group were significantly increased (P<0.05). This indicates that intragastric administration of AKKP to the CRC mice can increase the mRNA expression of caspase-9, Bid, and Bim in the colon tissue, thereby reducing the degree of intestinal injury.

The above results indicate that AKK PROBIO has a significant regulatory effect on colorectal carcinoma in mice, can alleviate AOM/DSS-induced body weight loss, reduction in colorectum length, and rise in spleen and liver indices of the mice to a certain extent, and effectively reduces the tumor number and the degree of rectum tissue damage in CRC mice. It can significantly reduce expressions of pro-inflammatory factors IL-1β, IL-6, IFN-γ, iNOS and NF-κB in the serum of the mouse. At the genetic level, it can significantly down-regulate mRNA expressions of p50, p52, p65, and IκBβ in colon tissue, up-regulate mRNA expressions of caspase-9, Bid and Bim in colon tissue, reduce the degree of intestinal inflammation, and influence occurrence and development of the colorectal carcinoma. In summary, AKK PROBIO has a good intervention effect on colorectal carcinoma.

Embodiment 4: Safety Evaluation of AKK PROBIO (AKK. Pro)

(1) Hydrophobicity

Based on the ability of bacteria to adhere to hydrocarbons, the cell surface hydrophobicity of strain AKK PROBIO was measured. A test of bacterial adherence to hydrocarbon (BATH) was conducted using xylene, and some modifications were made. Specifically, the strains were cultured overnight in a BHI medium at 37° C. Cells were collected by centrifugation (4° C.; 8000 rpm; 10 min), washed twice, and resuspended in a phosphate buffer (PBS, pH 7), and absorbance (OD600 nm) was adjusted to 0.5 to normalize bacteria number. Then, an equal volume of xylene was added and vortexed for 5 min to fully mix a two-phase system. After the incubation at room temperature for 15, 30, and 60 min, an aqueous phase was carefully removed, and its absorbance at 600 nm was measured using a spectrophotometer. The affinity (hydrophobicity) for the hydrocarbons was calculated using the following formula:

$$\text{Hydrophobicity } \% = \frac{P_0 - P_1}{P_0} \times 100$$

where P0 and P1 are absorbance values before and after extraction with the hydrocarbons, respectively.

Figure 11:
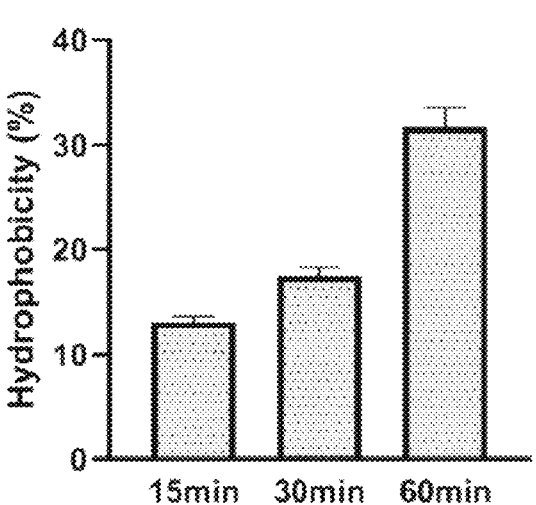
FIG. 11 shows a verification result of hydrophobicity of AKK PROBIO.

See FIG. 11 for the results. The results indicate that the hydrophobicity of AKK PROBIO rises with time and reaches 30% or above at 60 min.

(2) Auto-Aggregation

As described above, a cell suspension of the strain AKK PROBIO was prepared, and incubated at 37° C. The absorbance (OD600 nm) was adjusted to 0.5. Then the bacterial suspension was cultured at 37° C., and its absorbance at 600 nm at 4, 8, 12, 16, 20, and 24 h was measured. The auto-aggregation percentage was calculated using the following formula:

$$\text{Auto-aggregation } \% = 1 - \left(\frac{P_1}{P_0}\right) \times 100$$

Figure 12:
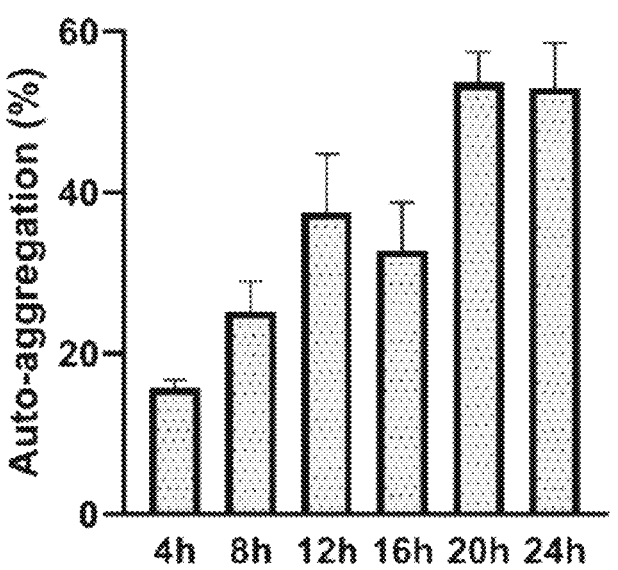
FIG. 12 shows a verification result of auto-aggregation of AKK PROBIO.

See FIG. 12 for the results. The results indicate that the auto-aggregation of strain rises with time and tends to stabilize at around 52% at 20 h.

(3) Tolerance to Gastrointestinal Juice

Gastric juice (5M HCl, 2 g/L NaCl, and 3.2 g/L pepsin, pH 2.0) and intestinal juice (6.8 g/L KH2 PO4, 10 g/L trypsin, and 0.1M NaOH, pH 8.0) were prepared, and then the gastric juice and the intestinal juice were filtered and sterilized using 0.22 μm sterile filter. AKK PROBIO activated twice in a 5 mL BHI liquid medium was centrifuged at 4000 rpm for 10 min to collect bacterial cells. The bacterial cells were washed twice with sterile saline and resuspended in 5 mL saline. A bacterial solution was mixed well with the sterile artificial gastric or intestinal juice in 1:1 (v/v). The mixture was shaken well, and then was placed in a constant-temperature incubator and culture was performed at 37° C. Viable counts were determined at 0 h and 3 h, respectively, and the survival rate of AKK PROBIO in the artificial gastric or intestinal juice was calculated by formula (1).

$$\text{survival rate } (\%) = \frac{3 \text{ h viable count}(CFU/\text{mL})}{0 \text{ h viable count}(CFU/\text{mL})} \times 100 \qquad \text{formula (1)}$$

Figure 13:
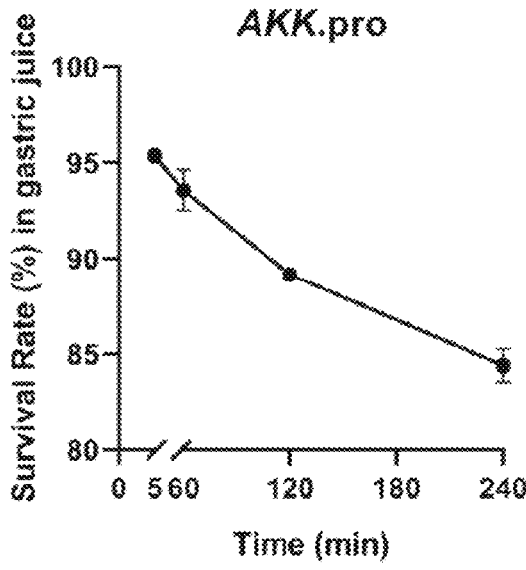
FIG. 13 shows a survival rate of AKK PROBIO in artificial gastric juice.
Figure 14:
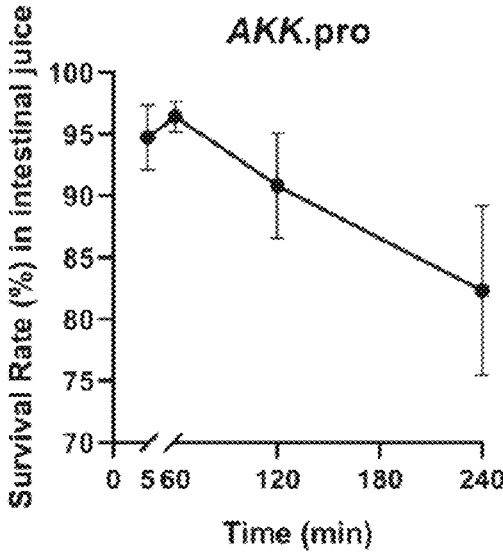
FIG. 14 shows a survival rate of AKK PROBIO in artificial intestinal juice.

See FIGS. 13 to 14 for the results. FIG. 13 shows that the survival rate of the strain in the gastric juice decreased over time, where the survival rate was around 85% at 240 min. FIG. 14 shows that the overall survival rate of the strain in the intestinal juice showed a declining trend, where the survival rate at 240 min was 80% or above.

(4) Biofilm Formation Ability

AKK PROBIO was cultured overnight in tryptone soy broth (TSB, Qingdao Hi-Tech Industrial Park HopeBio-Technology Co., Ltd, product number: HB4114) at 37° C. Then, bacterial cells were harvested by centrifugation at 4° C. at 8000 rpm for 10 min, washed twice with PBS, and resuspended in the following media: a TSB medium without glucose and TSB media supplemented with 0.25% glucose, 1% glucose, and 2.5% glucose, respectively. Three aliquots were taken from each bacterial suspension of 200 L, and loaded into 96-well plates. And cultured at 37° C. for 24 h with an uninoculated medium taken as a negative control. The medium in each well was sucked out, and washed three times with sterile saline to remove unattached cells. Remaining attached cells were fixed with 200 μL of methanol per well. After 15 min, liquid in the well was sucked out and the well was air-dried. Then staining was performed with 2% crystal violet for 5 min with 200 μL per well. Then washing was performed three times with sterile saline to remove excess stains. After the plate was air-dried, the attached cell were resuspended in 160 μL of 33% (V/V) glacial acetic acid, and its absorbance at 600 nm was measured. The critical value (ODC) was defined as an average OD value of the negative control. According to the OD values, the strains are classified as a non-biofilm producer (OD≤ODC), a weak producer (OD0<OD≤2×ODC), a moderate producer (2×ODC<OD≤4×ODC), or a strong biofilm producer (4×ODC<OD).

See Table 3 for the results.

TABLE 3

| AKK PROBIO Biofilm Formation | | | | |
|---|---|---|---|---|
| Strain | TSB 0% | TSB 0.25% | TSB 1% | TSB 2.5% |
| AKK PROBIO | WA | WA | WA | WA |

The data in Table 3 shows after incubation in TSB containing different concentrations of glucose (0%, 0.25%, 1%, and 2.5%) at 37° C. for 24 h, the critical value (ODC) was defined as an average OD value of the negative control. According to the OD values, the strains were classified as non adherent NA (OD≤ODC), weakly adherent WA (ODC<OD≤2×ODC), moderately adherent MA (2×ODC<OD≤4×ODC), and SA strongly adherent (4×ODC<OD). By determining the biofilm formation ability of the strain, it is judged that the biofilm formation ability of the strain is weak.

(5) Toxicological Evaluation 5.1. Bacterial Reverse Mutation Test

Bacterial strains used were *Salmonella typhimurium* TA97a (National Center for Type Culture Collection NTCC, 506391), *S. typhimurium* TA98 (NTCC, 506392), *S. typhimurium* TA100 (NTCC, 506395), *S. typhimurium* TA1535 (NTCC, 506396), and *Escherichia coli* WP2 uvrA (CHI Scientific, Co., Ltd., product number: 6-1705). To prepare a drug delivery formulation, distilled water was used as a carrier to prepare a suspension (100 mg/mL) for a test item. The test item (strain AKK PROBIO) may influence the test results in multiple ways, thus invalidating the study. Therefore, bacteria in samples for the test item were removed by a mechanical means. In the process of mixing the formulation, any soluble components for the test item was dissolved in the carrier, and then, residual bacteria were removed by centrifugation (4° C.; 8000 rpm; 10 min). After centrifugation, liquid supernatant was removed and sterile filtration was performed with a 0.22 μm filter. Then a lower-concentration formulation was prepared, and test bacterial strains were treated.

Based on the preliminary experimental results, initial mutation research (plate incorporation method) and confirmatory mutation research (pre-culture procedure) were conducted. In the confirmatory mutation research, detection was performed at 15.81, 50, 158.1, 500, 1581, and 5000 μg/plate. The maximum concentration was recommended by current regulations and guidelines. Positive control included fenaminosulf, sodium azide, methyl methylsulfonate, and 2-aminofluorene dissolved in distilled water or dimethyl sulfoxide. The survival rate of test bacterial cells was checked through plate experiments in each test. If there is a dosage-related increase in the number of revertants, it is considered that the test item has mutagenicity, and/or a reproducible biology-related positive reaction targeting at least one dosage group occurs in at least one strain with or without metabolic activation. If the number of reversions in the strains of *S. typhimurium* TA98 and *S. typhimurium* TA100, and *E. coli* WP2 uvrA is more than twice that of the negative control. it is considered that this increase is biologically related. The number of reversions in the strains of *S. typhimurium* TA97a and *S. typhimurium* TA1535 is more than three times higher than that of the negative control.

See FIG. 4 for the results.

TABLE 4

Number of revertant mutants per plate (mean ± standard deviation)

| | Salmonella typhimurium | | | | | | | | Escherichia coli | |
| | TA97a | | TA98 | | TA100 | | TA1535 | | WP2A | uvr |
| Groups | −S9 | +S9 | −S9 | +S9 | −S9 | +S9 | −S9 | +S9 | −S9 | +S9 |
|---|---|---|---|---|---|---|---|---|---|---|
| Negative control | 122.00 ± 30.68 | 126.20 ± 22.13 | 41.40 ± 8.11 | 35.00 ± 6.40 | 144.60 ± 25.52 | 109.00 ± 43.81 | 12.00 ± 4.42 | 16.00 ± 6.52 | 122.40 ± 19.36 | 162.00 ± 32.41 |
| AKK. pro | 98.20 ± 7.66 | 101.80 ± 7.66 | 36.80 ± 7.50 | 31.60 ± 6.77 | 61.6 0 ± 12.95 | 52.00 ± 9.64 | 10.00 ± 3.94 | 12.40 ± 2.97 | 113.60 ± 5.77 | 130.80 ± 8.38 |
| Positive control 1 | 1169.4 ± 181.47 | — | 1525.00 ± 271.69 | — | — | — | — | — | — | — |
| Positive control 2 | — | — | — | — | 1347.00 ± 202.27 | — | — | — | 613.40 ± 61.99 | — |
| Positive control 3 | — | — | — | — | — | — | 141.80 ± 26.63 | — | — | — |
| Positive control 4 | — | 1288.40 ± 296.29 | — | 1398.60 ± 309.13 | — | 1247.40 ± 59.71 | — | 163.20 ± 9.98 | — | 548.60 ± 111.81 |

Note:
Drugs for positive controls 1 to 4: fenaminosulf, methyl methylsulfonate, sodium azide, and 2-aminofluorene.

The results of the bacterial reverse mutation test show that the strain has no mutagenicity.

5.2. Acute Toxicity

To access the acute toxicity of the strain AKK PROBIO, SPF Kunming mice (7-week-old, half male and half female, weighing 10 g to 18 g) were randomly divided into four groups (n=8). The mice in each group were intragastrically administered orally with a suspension (0.5 mL, with normal saline as a solvent) containing $1\times10^9$, $5\times10^{10}$ or $5\times10^{11}$ CFU/d of strain AKK PROBIO or 0.5 mL/d of normal saline for 1 d. The groups were recorded as a sodium chloride solution group, a low dosage group, a medium dosage group and a high dosage group, respectively, and the general conditions and the body weight were observed per day within 7 to 10 d. At the end of the experimental period, blood samples were collected for hematological and serum biochemical analysis (refer to Embodiment 4). A histopatho-logical examination of major organs and tissue was performed on all animals in each group (refer to Embodiment 4).

Figures 15, 15A, 15B, 15C:
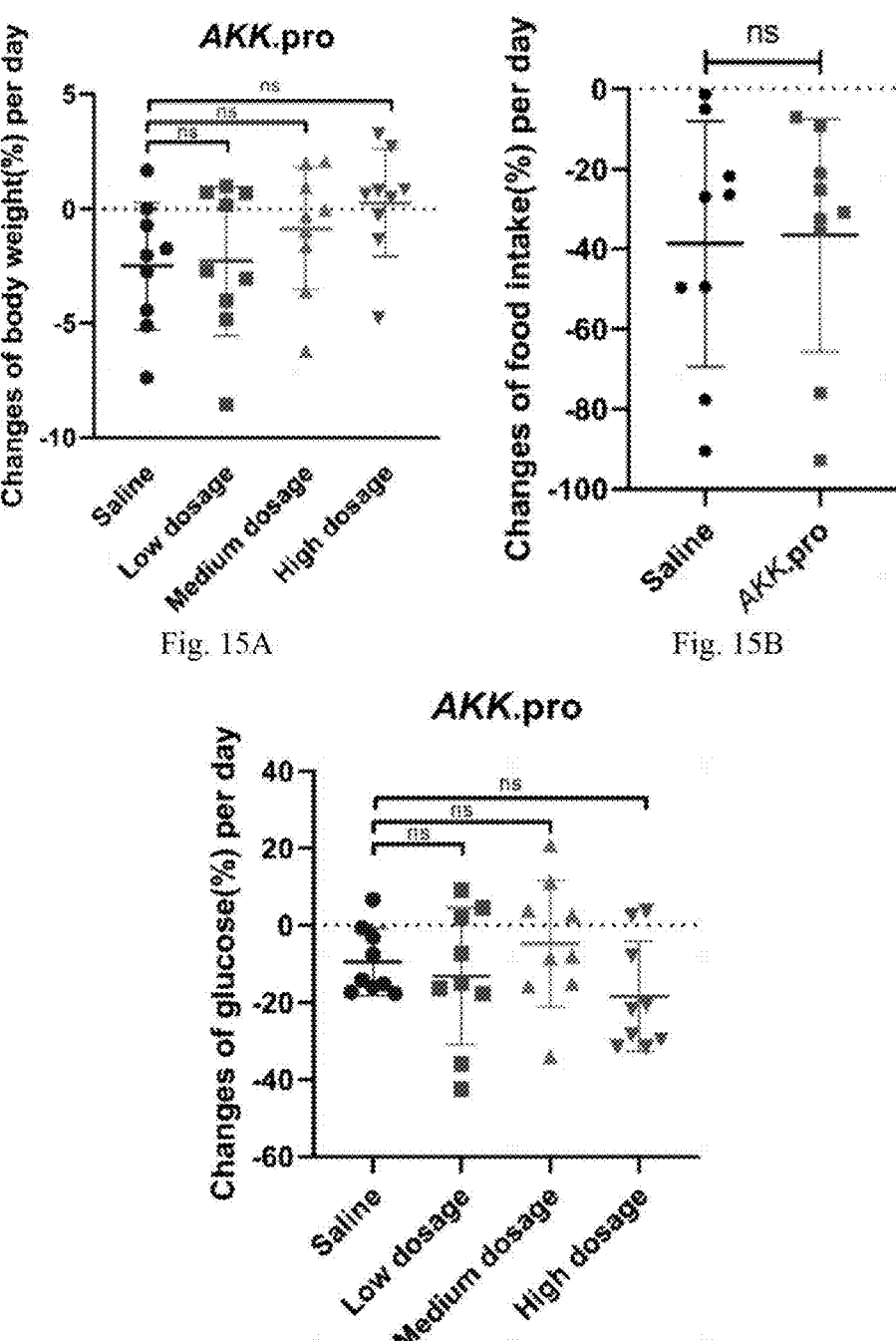
FIG. 15 shows results of changes of body weight (FIG. 15A), changes of food intake (FIG. 15B) and changes of blood (FIG. 15C) glucose in mice in acute toxicity experiments.

See FIG. 15 for the results of changes of body weight, changes of food intake and changes of blood glucose in mice. The results show that no death occurs in the mice after acute intragastric administration of high-dosage AKK. pro, medium-dosage AKK. pro and low-dosage AKK. pro. There was no significant difference between the mice in a test group and the mice in a control saline group in changes of body weight per day. During the acute intragastric administration, there was no significant difference between test mice and the mice in the control saline group in changes of food intake per day. During the acute intragastric administration, there was no significant difference between the test mice and the mice in the control saline group in changes of blood glucose per day.

See Table 5 for the blood routine examination results of the mice.

TABLE 5

Blood Routine Examination of mice intragastrically administrated with high-dosage AKK. pro, medium-dosage AKK. pro, and low-dosage AKK. pro

| | | Sodium chloride solution | Low dosage | Medium dosage | High dosage | Reference interval | Unit |
|---|---|---|---|---|---|---|---|
| While blood cells | WBC | 0.40 ± 0.25 | 0.88 ± 0.65 | 1.06 ± 0.55 | 0.54 ± 0.37 | 0.8-6.8 | 10^9/L |
| Red blood cells | RBC | 1.30 ± 0.78 | 2.12 ± 0.64 | 2.28 ± 1.09 | 1.38 ± 0.35 | 6.36-9.42 | 10^12/L |
| Hemoglobin | HGB | 85.83 ± 25.30 | 87.50 ± 26.16 | 96.00 ± 14.14 | 110.00 ± 11.31 | 110-143 | g/L |
| Mean corpuscular volume | MCV | 54.73 ± 4.23 | 55.90 ± 2.97 | 53.05 ± 7.85 | 52.60 ± 7.07 | 48.2-58.3 | fL |
| Platelets | PLT | 1128.83 ± 488.34 | 921.00 ± 760.85 | 891.50 ± 516.90 | 1112.50 ± 344.36 | 450-1590 | 10^9/L |
| Lymphocyte number | Lym# | 0.40 ± 0.25 | 0.82 ± 0.57 | 0.99 ± 0.45 | 0.54 ± 0.37 | 0.7-5.7 | 10^9/L |
| Middle cell number | Mid# | 0 ± 0 | 0.01 ± 0.01 | 0.01 ± 0.01 | 0 ± 0 | 0-0.3 | 10^9/L |
| Granulocyte number | GR# | 0 ± 0 | 0.05 ± 0.07 | 0.06 ± 0.08 | 0 ± 0 | 0.1-1.8 | 10^9/L |
| Lymphocyte percentage | Lym % | 100 ± 0 | 95.55 ± 6.29 | 95.20 ± 6.79 | 100 ± 0 | 55.8-90.6 | % |

TABLE 5-continued

Blood Routine Examination of mice intragastrically administered with
high-dosage AKK. pro, medium-dosage AKK. pro, and low-dosage AKK. pro

| | | Sodium chloride solution | Low dosage | Medium dosage | High dosage | Reference interval | Unit |
|---|---|---|---|---|---|---|---|
| Middle cell percentage | Mid % | 0 ± 0 | 0.65 ± 0.92 | 0.60 ± 0.85 | 0 ± 0 | 1.8-6 | % |
| Granulocyte percentage | GR % | 0 ± 0 | 3.8 ± 5.37 | 4.20 ± 5.94 | 0 ± 0 | 8.6-38.9 | % |
| Platelet-large cell ratio | PLCR | 26.77 ± 5.39 | 27.65 ± 4.88 | 18.00 ± 0.71 | 19.70 ± 0.28 | 13-50 | % |
| Platelet-large cell count | PLCC | 314.5 ± 170.46 | 273.50 ± 255.27 | 158.50 ± 86.97 | 218.50 ± 64.35 | 10-100 | 10^9/L |
| Hematocrit | HCT | 7.27 ± 4.31 | 11.70 ± 2.97 | 11.70 ± 3.96 | 7.35 ± 2.76 | 34.6-44.6 | % |
| Mean corpuscular-hemoglobin concentration | MCHC | 1667.50 ± 1033.17 | 802.00 ± 427.09 | 892.00 ± 422.85 | 1579.00 ± 438.41 | 302-353 | g/L |
| Red blood cell distribution width coefficient of variation | RDW_CV | 14.47 ± 2.27 | 14.85 ± 3.04 | 13.05 ± 4.31 | 13.75 ± 2.47 | 11-17 | % |
| Red blood cell distribution width standard deviation | RDW_SD | 79.93 ± 17.50 | 76.40 ± 17.82 | 73.40 ± 29.70 | 92.55 ± 6.58 | 33-50 | fL |
| Mean corpuscular hemoglobin | MCH | 88.90 ± 47.55 | 45.35 ± 26.23 | 49.20 ± 29.70 | 81.55 ± 12.37 | 15.8-19 | pg |
| Mean platelet volume | MPV | 9.43 ± 0.42 | 9.55 ± 0.35 | 9.15 ± 0.78 | 9.20 ± 0.71 | 3.8-6 | fL |
| Plateletcrit | PCT | 1.07 ± 049 | 0.89 ± 0.76 | 0.84 ± 0.54 | 1.04 ± 0.40 | 0.15-0.3 | % |
| Platelet distribution | PDW | 20.42 ± 1.41 | 19.10 ± 1.70 | 20.15 ± 1.20 | 21.00 ± 0.28 | 15-17 | % |

The data in Table 5 indicate that there is no significant difference between the mice in an acute intragastric administration group and the mice in the control saline group in various blood indicators.

Figures 16, 16A, 16B, 16C, 16D, 16E, 16F:
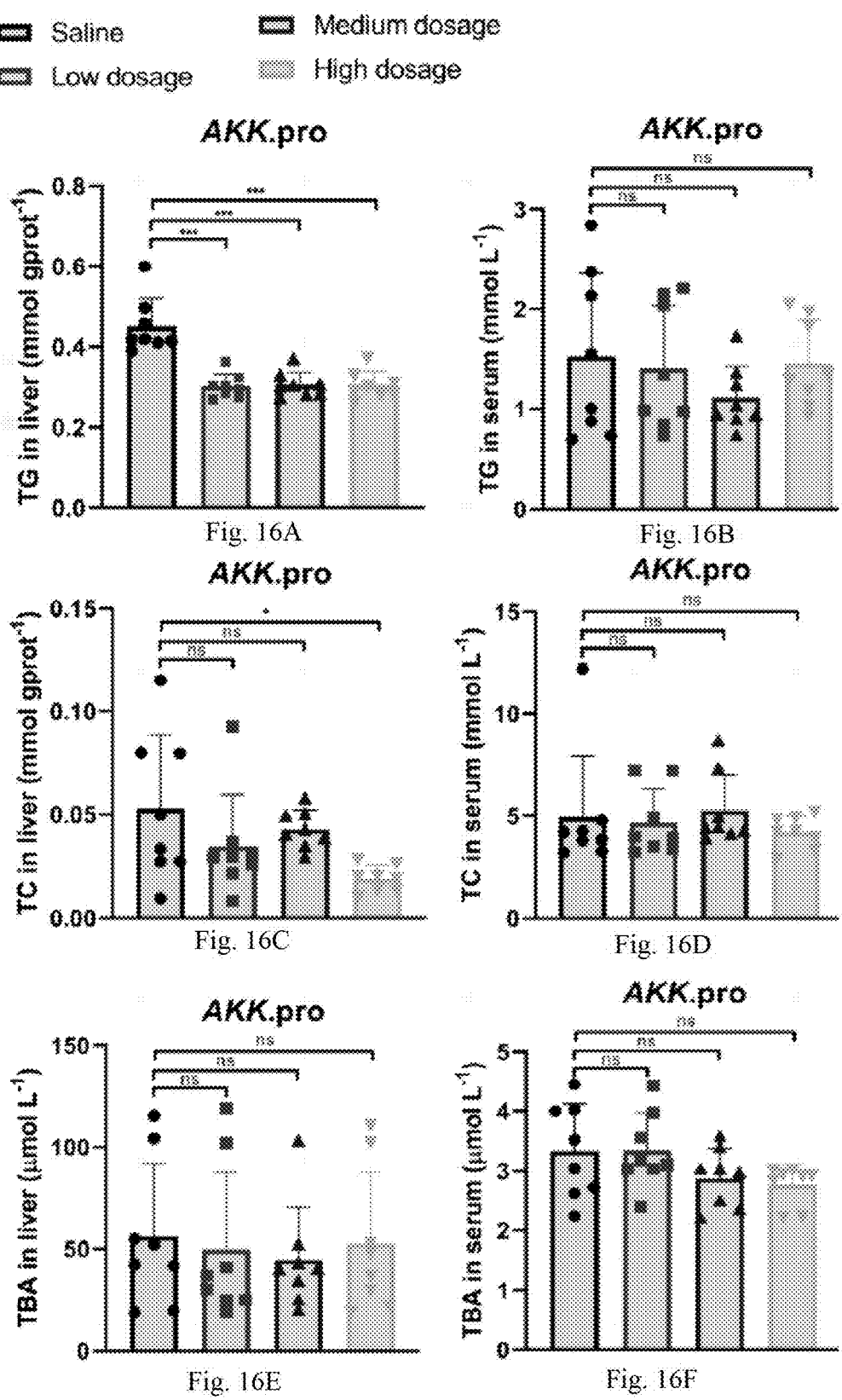
FIG. 16 shows detection results of the content of triglyceride (TG, FIG. 16A shows TG in liver, FIG. 16B shows TG in serum), the content of cholesterol (TC, FIG. 16C shows TC in liver, FIG. 16D shows TC in serum), and the content of bile acid (TBA, FIG. 16E shows TBA in liver, FIG. 16F shows TBA in serum) in mice in acute toxicity experiments.

See FIG. 16 for the detection results of the content of triglyceride (TG), the content of cholesterol (TC), and the content of bile acid (TBA) in the mice. The results show that the level of triglyceride in the liver of the test mouse is significantly lower than that of the mouse in the control saline group. There was no significant difference between test mice and control mice in level of the triglyceride in serum. There was no significant difference between the test mice and the mice in the control group in level of the cholesterol and the level of the bile acid in both serum and liver.

Figure 17:
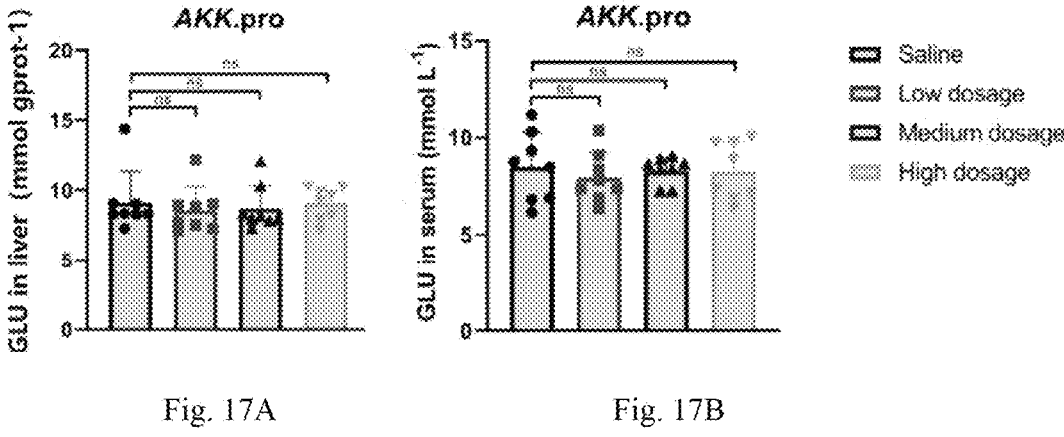
FIG. 17 shows detection results of the level of glucose (GLU, FIG. 17A shows GLU in liver, FIG. 17B shows GLU in serum) in mice in acute toxicity experiments.
Figure 18:
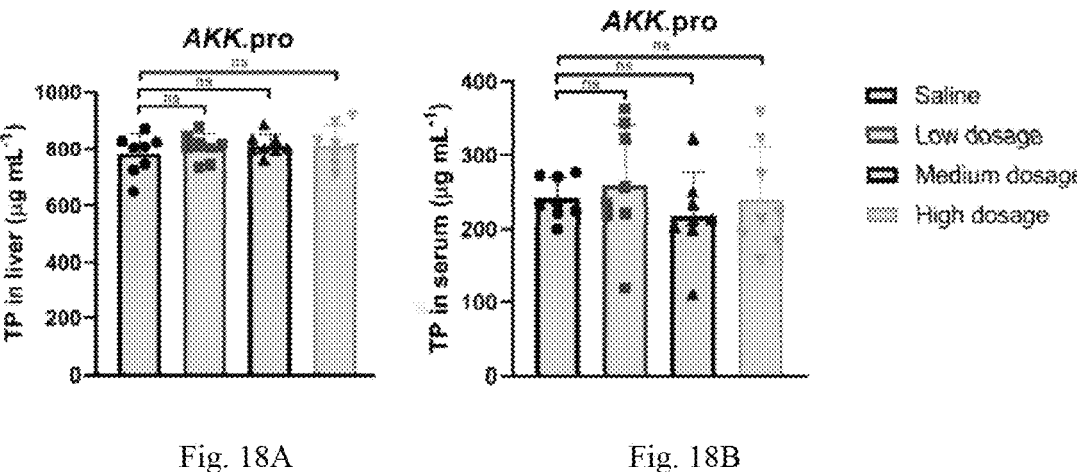
FIG. 18 shows detection results of the level of total protein (TP, FIG. 18A shows TP in liver, FIG. 18B shows TP in serum) in mice in acute toxicity experiments.
Figures 19, 19A, 19B:
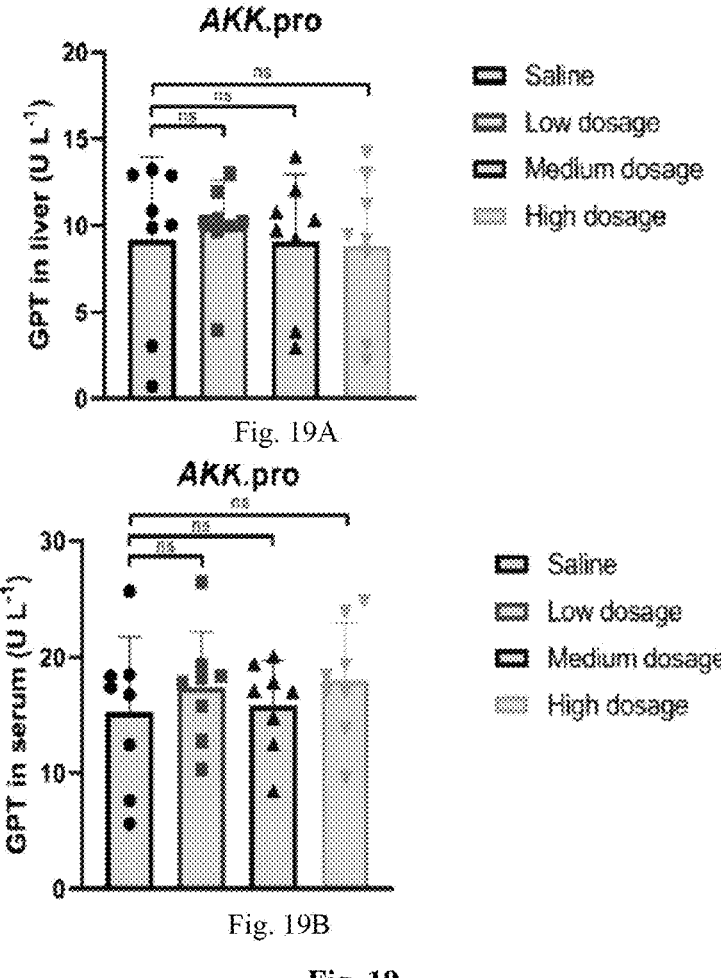
FIG. 19 shows detection results of the activity of glutamic pyruvate transaminase (GPT, FIG. 19A shows GPT in liver, FIG. 19B shows GPT in serum) in mice in acute toxicity experiments.

There was no significant difference between the test mice and the mice in the control group in level of glucose (GLU) in both serum and liver, as shown in FIG. 17. There was no significant difference between the test mice and the mice in the control group in level of total protein (TP) in both serum and liver, as shown in FIG. 18. There was no significant difference between the test mice and the mice in the control group in activity of glutamic pyruvate transaminase (GPT) in both serum and liver, as shown in FIG. 19. There was no significant difference between the test mice and the mice in the control group in activity of glutamic oxalacetic transaminase (GOT) in both serum and liver, as shown in FIG. 20. There was no significant difference between the test mice and the mice in the control group in content of creatinine (GRE) in serum, as shown in FIG. 21. There was no significant difference between the test mice and the mice in the control group in concentration of blood urea nitrogen (BUN) in serum, as shown in FIG. 22.

The comparison results of organ indices show that there was substantially no significant difference between the test mice and the mice in the control group in weight of major organs such as heart, liver, spleen, kidneys, thymus, brain, testes, lungs, stomach, and intestine.

See FIG. 23 for pathological sections of livers and kidneys of the mice. There was no significant pathological injury to the livers and kidneys of the test mice and the mice in the control group.

5.3. Subchronic Toxicity experiment

Animals were randomly divided into four groups: group 1 (half male and half female) (saline, 0 CFU/kg. bw/d), group 2 (half male and half female) ($9.2 \times 10^8$ CFU/kg. bw/d), group 3 (half female and half male) ($27.6 \times 10^8$ bw/d), and group 4 (half male and half female) ($92 \times 10^8$ CFU/kg. bw/d). A new bacterial suspension was prepared per day. The bacterial suspension was intragastrically administered orally for 90 consecutive days at a dosage volume of 5 mL/kg. bw. Clinical signs were recorded per day, and detailed clinical observation was conducted once a week. The body weight, the food consumption, and the water intake were recorded once a week. At the end of the experimental period, blood samples were collected for hematological and serum biochemical analysis (refer to Embodiment 4). An autopsy was conducted on all animals, and the weight of main organs was recorded. A histopathological examination was performed on the major organs and tissue of all the animals in each group (refer to Embodiment 4).

Method for Detecting Glucose Tolerance in Mice:

Before the start of the experiment, mice needed to fast for 12 to 16 h, but there was still a water supply. Preparation of glucose solution: generally, 25% glucose solution at 2 g/kg. bw was prepared, and the desired amount of glucose was calculated according to the body weight of a mouse.

Determination of basal blood glucose: Before the start of the experiment, the basal blood glucose level of the mouse was measured using a blood glucose meter or other blood glucose determination methods. Generally, tail venous blood of the mouse was measured.

Glucose loading administration: The glucose solution was intragastrically administered to the mouse.

Determination of blood glucose: In a certain time interval after administration, at 0, 15, 30, 60, 90 and 120 min, the tail venous blood of the mouse was taken, and the blood glucose level of the mouse was measured using a blood glucose meter measurement method.

Method for Detecting Insulin Tolerance in Mice:

Preparation of insulin solution: an appropriate concentration of insulin solution was prepared, generally, an insulin injection was used, and the desired amount of insulin for each mouse was calculated according to 0.5 U/kg. bw. Insulin injection: The insulin solution was administered subcutaneously to the mice in the experimental group. The mice in the control group were not subjected to this treatment. Determination of blood glucose: In a certain time interval after administration, at 0, 15, 30, 60, 90 and 120 min, the tail venous blood of the mouse was taken, and the blood glucose level of the mouse was measured using a blood glucose meter measurement method.

Figure 24:
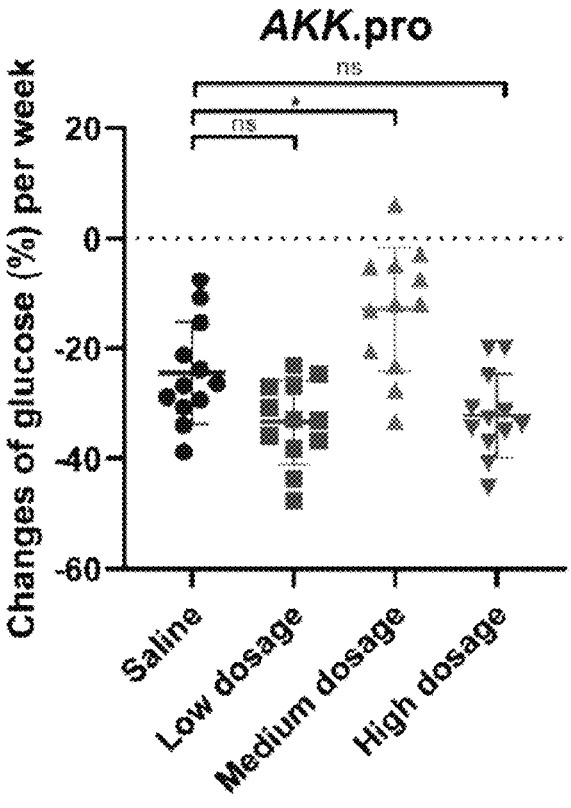
FIG. 24 shows blood glucose changes of mice in sub-chronic toxicity experiments.
Figure 25:
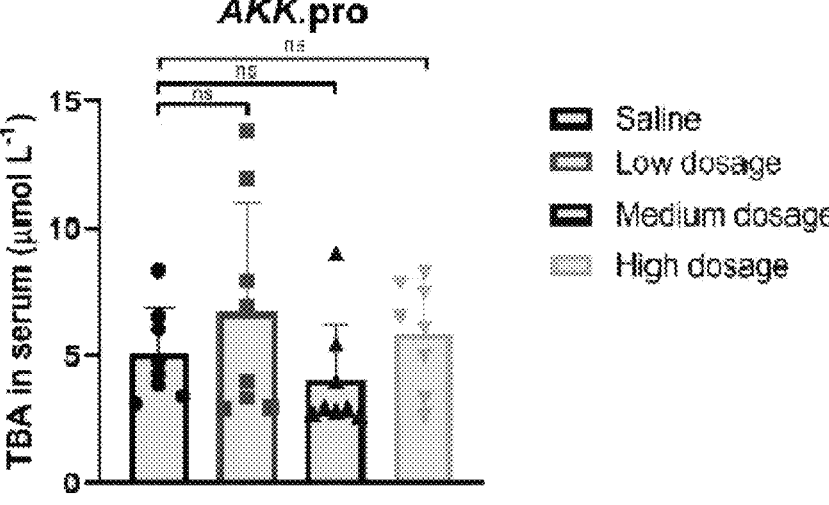
FIG. 25 shows bile acid levels of livers of mice in subchronic toxicity experiments.

The test results show that no death occurs in the mice after intragastric administration of high-dosage AKK. pro, medium-dosage AKK. pro and low-dosage AKK. pro for 90 consecutive days. There was no significant difference between the mice in a test group and the mice in a control saline group in changes of body weight per week. During the consecutive intragastric administration, there is no significant difference between test mice and the mice in the control saline group in changes of food intake per week. During the consecutive intragastric administration, there was a significant difference between mice in a medium-dosage intragastric administration group and the mice in the control saline group in changes of blood glucose per week, while there was no significant difference between the other groups and the control group (See FIG. 24). There was no significant difference between the mice in the intragastric administration group and the mice in the control saline group in various blood indicators. There was no significant difference between the test mice and the mice in the control group in level of the triglyceride and the level of the cholesterol in both liver and serum. There was a significant difference between the mice in the medium dosage group and the mice in the control group mice in level of the bile acid in liver (FIG. 25), while there was no significant difference between the other groups and the control group in level of the bile acid both in serum and liver. There was no significant difference between the test mice and the mice in the control group in level of glucose, content of total protein, activity of glutamic pyruvate transaminase, and activity of glutamic oxalacetic transaminase in both serum and liver. There was no significant difference between the test mice and the mice in the control group in content of creatinine and concentration of blood urea nitrogen in serum. There was substantially no significant difference between the test mice and the mice in the control group in weight of major organs such as heart, liver, spleen, kidneys, thymus, brain, testes, lungs, pancreas, stomach, and intestine. There was no significant pathological injury to the livers and kidneys of the test mice and the mice in the control group. There was no significant difference between the test mice and the mice in the control group in blood glucose regulation ability (glucose tolerance and insulin tolerance).

(6) Drug Sensitivity Analysis

Referring to the Clinical and Laboratory Standards Institute (CLSI) method [CLSI. Performance Standards for Antimicrobial Susceptibility Testing; 26th ed. CLSI supplement M100S. Wayne, PA, USA: Clinical and Laboratory Standards Institute; 2016.], drug sensitivity determination was performed on AKK PROBIO.

*Bacteroides fragilis* ATCC 25285 was selected as a quality-control strain.

Main Reagents and Media:

*Brucella agar* medium and *Brucella* broth medium: purchased from the BD company; AnacroPack: purchased from the Mitsubishi Corporation; sheep blood: purchased from the Shanghai Kangrun Biological Technology Co., Ltd.; chlorhematin: purchased from SINOPHARM; Vitamin K1: purchased from Sigma; ampicillin, ceftriaxone, cefotaxime, meropenem, and tetracycline: purchased from the National Institute for the Control of Pharmaceutical and Biological Products; and moxifloxacin and chloramphenicol: purchased from the European Pharmacopoeia.

The sensitivity of AKK PROBIO to ampicillin, ceftriaxone, cefotaxime, meropenem, tetracycline, moxifloxacin, and chloramphenicol was determined using an agar dilution method recommended by CLSI. The quality-control strain *B. fragilis* ATCC 25285 was determined using a micro broth dilution method recommended by CLSI.

Drug Sensitive Test Results:

As can be seen from Table 6, the strain AKK PROBIO to be tested was sensitive to ampicillin, ceftriaxone, cefotaxime, meropenem, tetracycline, moxifloxacin, chloramphenicol.

TABLE 6

| Drug Sensitive Test Results of AKK PROBIO | | | | | | | | |
| --- | --- | --- | --- | --- | --- | --- | --- | --- |
| | | | | | | Quality-control strain *Bacteroides fragilis* ATCC25285 | | |
| | | | | Test strain AKK PROBIO | | Quality | | Within quality control |
| | Judgment criterion | | | MIC | Judgment | control | MIC | range |
| Antibiotics | S | I | R | (ug/mL) | result | range | (ug/mL) | or not |
| Ampicillin | ≤0.5 | 1 | ≥2 | <0.25 | Sensitive | 16-64 | 64 | Yes |
| Ceftriaxone | ≤16 | 32 | ≥64 | 8 | Sensitive | 32-128 | 128 | Yes |
| Cefotaxime | ≤16 | 32 | ≥64 | 16 | Sensitive | 8-32 | 32 | Yes |
| Meropenem | ≤4 | 8 | ≥16 | 0.125 | Sensitive | 0.03-0.25 | 0.25 | Yes |
| Tetracy cline | ≤4 | 8 | ≥16 | 2 | Sensitive | 0.125-0.5 | 0.5 | Yes |
| Chloramphenicol | ≤8 | 16 | ≥32 | 4 | Sensitive | 2-8 | 8 | Yes |

Embodiment 5: Alleviating Effect of AKK PROBIO on Alzheimer's Disease in APP/PS1 Double Transgenic Mice 20 12-month-old APP/PS1 double transgenic mice (Hangzhou Ziyuan Experimental Animal Technology Co., Ltd., batch MJ0324-058) were randomly divided into two groups: an APP group and an APP+AKK group, with 10 mice in each group. Another 10 littermate wild-type C57 BL/6J mice were taken as blank, which served as a WT group. All mice were given intragastric administration and injection for 30 d at 12-month age (see Table 7 for intragastric administration conditions). After all the experiments ended, blood was collected from the orbital veins of the mice. The mice were sacrificed by cervical dislocation. Part of brain tissue, liver tissue and colon tissue of the mice were taken and placed in 4% paraformaldehyde, and the remaining tissue was placed in an ultra-low temperature freezer at −80° C. for storage.

TABLE 7

| Intragastric Administration Group and Dosage | |
| --- | --- |
| Groups | Intragastric Administration |
| WT | Intragastric administration of the same amount of DDW and injection of the same volume of saline per day |
| APP | Intragastric administration of the same amount of DDW and injection of the same volume of saline per day |
| APP + AKK PROBIO | intragastric administration of AKK PROBIO solution with a concentration of $1 * 10^9$ CFU/mouse/d and injection of the same volume of saline per day |

DDW: Double distilled water. Preparation of AKK PRO-BIO bacterial suspension: 5 mL of AKK PROBIO cryopreserved bacterial solution was taken for activated culture; the cultured bacterial solution was centrifuged at 4000 r/min for 10 min; the centrifuged bacterial solution was washed twice, and then 5 mL of saline was added after washing to form a bacterial suspension with a concentration of $1*10^9$ CFU/mL. (1)

After administration, a Morris water maze experiment of a 4-day duration was conducted firstly. The water maze consists of a circular pool (with a diameter of 120 cm) and is evenly divided into four quadrants. During the experi-ment, the mice were moved into a laboratory two hours in advance to acquaint themselves with the environment. The water temperature was adjusted to around 21° C. to 22° C., and then milk was poured into the pool to make the water milky white. D1 to D3 were a training period, during which the mice were gently placed into the water from first, second, third, and fourth quadrants with their faces towards the direction of the pool wall reminders. Swimming trajectories at 1 min were recorded. Mice that do not find a platform within specified time needed to be guided to the platform. Each mouse was trained once per day per quadrant for 3 consecutive days. D4 was an experimental period, during which a quadrant was randomly selected for each mouse and then the mice were placed in the pool. The time required to find the platform within 60 s, i.e., escape latency, was recorded, and the swimming trajectory of each mouse was recorded with a video acquisition system. If the mouse fail to find the platform within 60 s after entering the water, the escape latency is recorded as 60 s.

(2) Determination of Levels of Hippocampus Aβ, Inflammatory Factors and Chemokines in AD Mice Analysis of Protein Expression of Hippocampus Aβ

A hippocampus was homogenized in 1 mL RIPA (Thermofisher, Waltham, MA, USA) and 10 μL PMSF (Thermofisher), and the homogenized hippocampus was centrifuged at 4° C. at 12000×g for 5 min. Proteins were quantified using a BCA protein assay kit (Thermofisher). A protein sample was mixed with a sample buffer (Thermofisher) in a ratio of 4:1, and the mixture was heated at 95° C. for 5 min. Then the sample was dispensed into gel pores of SDS-PAGE gel and the gel was run at 100 V. Strips on SDS-PAGE gel were transferred onto a PVFD membrane. The PVDF membrane was sealed with 5% skim milk for 1 h, and then the stripes were incubated overnight with a primary antibody (Thermofisher) at 4° C. An antibody (Thermofisher) was added after the membrane was washed and the incubation was performed for 1 h. Images on iBright™ (Thermofisher) were obtained after chemiluminescence was performed using a western ECL substrate (Thermofisher), where the images were used for subsequent analysis.

Determination of Levels of Inflammatory Factors and Chemokines

The hippocampus was taken and homogenized with PBS, and then liquid supernatant was drawn for the experiment. The levels of IL-4 (interleukin-4, Nanjing Jiancheng Biological Engineering Research Institute, product number:

H005-1-2), IL-10 (interleukin-10, Nanjing Jiancheng Biological Engineering Research Institute, product number: H009-1-2), CCL2 (chemokine ligand 2, Nanjing Jiancheng Biological Engineering Research Institute, product number: H318-1) and CXCL1 (CXC chemokine ligand 1, Nanjing Jiancheng Biological Engineering Research Institute, product number: H306-1) in the hippocampus were tested by the instruction of the ELISA kit.

(3) Data Analysis

Tissue samples were measured in parallel three times, and then a mean was calculated. The data was averaged and analyzed using SPSS software (SPSS v. 25 for Windows, IBM Software Group, Chicago, IL, USA). Differences between the means of the groups were assessed using Duncan multiple-range test by one-way ANOVA. A difference of $p < 0.05$ was considered statistically significant.

(4) Experimental Results

Figure 26:
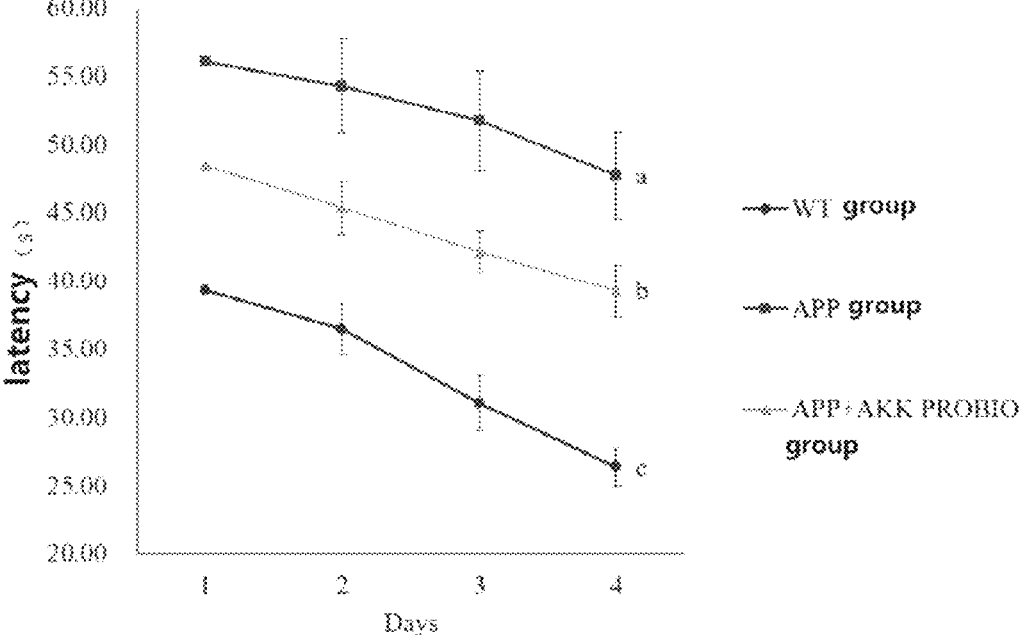
FIG. 26 shows analysis results of Morris water maze experiments on APP/PS1 double transgenic mice (Alzheimer's disease).

The analysis of Morris water maze results is as shown in FIG. 26. After 4 consecutive days of Morris water maze training, the escape latency of the mouse in each group showed a decreasing trend. Compared with the mice in the APP group, the mice in the APP+AKK PROBIO group had a shortened escape latency and a significantly shortened path to finding the platform.

See Table 8 for the analysis of inflammatory indicators in the AD mice. The levels of CXCL1 and CCL2 in the hippocampus in the WT group were minimum among the four groups, while the levels of IL-4 and IL-10 were maximum among the four groups. The levels of IL-4 and IL-10 in the APP group were minimum among the four groups, while the levels of CXCL1 and CCL2 were maximum among the four groups. The levels of CXCL1 and CCL2 in the APP+AKK group showed a declining trend compared with those in the APP group, while the levels of IL-4 and IL-10 showed a rising trend compared with those in the APP group. This indicates that the purpose of clearing Aβ can be achieved by AKK PROBIO by up-regulating the levels of Aβ degrading enzyme IDE and anti-inflammatory factors IL-4 and IL-10, thereby alleviating Alzheimer's disease in the APP/PS1 double transgenic mice.

Medicines and Reagents:

monosodium urate (2,6,8-trihydroxypurine) and glucosamine sulfate, purchased from the Sigma Corporation, USA; ELISA kit for IL-6, IL-10, IL-1β, and TNF-α purchased from Thermo Fisher, USA; assay kit for the activity of myeloperoxidase (MPO), superoxide dismutase (SOD), reduced glutathione (GSH), and assay kit for the content of malondialdehyde (MDA), purchased from the Nanjing Jiancheng Technology Co., Ltd.

Experimental Grouping and Sample Treatment:

Mice were randomly divided into 5 groups: a normal group, a model group, a glucosamine sulfate (positive control) group, an Akk low-concentration experimental (Akk-L) group, and an Akk high-concentration experimental (Akk-H) group, with 10 mice in each group. The mice in the normal group and the mice in the model group were intragastrically administered with distilled water at a dosage of 0.1 mL/10 g. bw per day. The mice in the glucosamine sulfate group were intragastrically administered with glucosamine sulfate at a dosage of 195 mg/kg. bw. The mice in the Akk-L group and the mice in the Akk-H group were intragastrically administered with Akk experimental bacteria at a dosage of $10^8$ CFU/kg. bw and $10^9$ CFU/kg. bw, respectively, for 7 consecutive days. Then, all experimental mice were anesthetized with isoflurane, and then 50 μL of PBS solution was injected into the tibiotarsal joint (ankle joint) of the right paw of the mouse in the normal group. 50 mg of sodium urate was added to 1 mL of PBS buffer to prepare a suspension. 50 μL of suspension was injected into the tibiotarsal joints (ankle joint) of the right paws of the rest of the mice except the mice in the model group to induce gouty arthritis. After the mice woke up, they were intragastrically administrated with a corresponding sample for 7 d

TABLE 8

| | | Content of Inflammatory Indicators in AD Mice | | |
| --- | --- | --- | --- | --- |
| | | WT | APP | APP + AKK PROBIO |
| Hippocampus | IL-4 | $410.91 \pm 0.36^a$ | $54.73 \pm 10.33^d$ | $210.90 \pm 19.77^c$ |
| | IL-10 | $3373.80 \pm 69.05^a$ | $1035.86 \pm 35.64^d$ | $2516.88 \pm 91.80^c$ |
| | CXCL1 | $355.37 \pm 7.50^c$ | $1217.20 \pm 144.70*$ | $653.77 \pm 15.44^b$ |
| | CCL2 | $103.32 \pm 1.86^c$ | $159.11 \pm 6.11$ | $123.20 \pm 0.50^b$ |
| | Aβ | $59.23 \pm 13.57^c$ | $348.45 \pm 42.59^4$ | $185.15 \pm 9.07^b$ |
| Serum | IL-4 | $106.52 \pm 6.45^a$ | $35.00 \pm 1.27^4$ | $70.42 \pm 3.40^c$ |
| | IL-10 | $2779.61 \pm 206.20^a$ | $565.36 \pm 44.3sd$ | $2133.04 \pm 18947^b$ |
| | CXCL1 | $14.87 \pm 0.50^c$ | $168.91 \pm 42.28$ | $56.40 \pm 2.88^b$ |
| | CCL2 | $59.07 \pm 0.11^{\ d}$ | $80.13 \pm 1.73^4$ | $67.74 \pm 1.51^b$ |

As for a to d, the same lowercase letter indicates no significant difference between two corresponding groups, while different lowercase letters indicate significant differences between the two corresponding groups ($p < 0.05$).

Embodiment 6: Functional Verification of AKK PROBIO in Gouty Arthritis Mouse Model Experimental Animals:

50 6-week-old male BALB/c mice (20 to 22 g), purchased from the Shanghai SLAC Laboratory Animal Co., Ltd.

still at the dosage of the sample intragastrically administrated in the previous 7 days.

(1) Determination of Oxidized State of Mouse Ankle Joint Tissue:

0.1 g of mouse ankle joint tissue was weighed and added into liver tissue containing 0.9 mL of saline and mixing was performed. Subsequently, mixed tissue samples were centrifuged at a speed of 4000 rpm for 10 min to obtain liquid supernatant. Next, related indicators in the liquid supernatant of a tissue homogenate was determined using assay kits for MPO, SOD, GSH, and MDA. See FIG. 9 for the results.

TABLE 9

Activity of MPO, SOD, and GSH and Level of MDA in
Mouse Ankle Joint Tissue

| Group | MPO (U/g) | SOD (U/mg) | GSH (mg/g) | MDA (nmol/mg) |
|---|---|---|---|---|
| Normal group | 0.38 ± 0.03 | 6.07 ± 0.06 | 47.05 ± 2.05 | 5.74 ± 075 |
| Model group | 2.49 ± 0.19 | 1.07 ± 0.38 | 18.06 ± 2.23 | 26.69 ± 1.71 |
| Glucosamine sulfate group | 1.82 ± 0.17 | 2.50 ± 0.40 | 31.14 ± 1.66 | 20.31 ± 1.52 |
| Akk-L group | 1.97 ± 0.19 | 2.31 ± 0.43 | 29.89 ± 2.63 | 20.93 ± 1.30 |
| Akk-H group | 0.77 + 0.06 | 4.70 ± 0.16 | 39.28 ± 2.39 | 12.97 ± 1.20 |

As for a to c, the same lowercase letter indicates no significant difference between two corresponding groups, while different lowercase letters indicate significant differences between the two corresponding groups ($p < 0.05$).

(2) Determination of Inflammatory Cytokines in Serum of Mice:

A taken-out whole blood sample of the mouse was centrifuged at 4° C. at 4000 rpm for 10 min to obtain supernatant serum. Serum-related inflammatory indicators were determined using the ELISA kit for IL-6, IL-10, IL-1β, and TNF-α. See FIG. 10 for the results.

TABLE 10

Levels of Cytokines (IL-6, IL-10, IL-1β, and TNF-α) in Serum of Mice

| Groups | IL-6 (ng/mL) | IL-10 (ng/ml) | IL-1β (ng/ml) | TNF-α (ng/ml) |
|---|---|---|---|---|
| Normal group | 52.97 ± 0.33 | 27.20 ± 1.17 | 12.66 ± 0.91 | 117.58 ± 5.44 |
| Model group | 90.05 ± 8.84 | 36.03 ± 1.92 | 24.97 ± 1.98 | 249.41 ± 19.94 |
| Glucosamine sulfate group | 66.85 ± 4.90 | 32.84 ± 1.94 | 21.15 ± 1.22 | 204.43 ± 15.32 |
| Akk-L group | 71.59 ± 5.46 | 34.17 ± 2.18 | 21.83 ± 1.72 | 211.76 ± 10.58 |
| Akk-H group | 58.83 ± 2.60 | 28.72 ± 1.35 | 18.48 ± 1.34 | 148.87 ± 9.60 |

As for a to d, the same lowercase letter indicates no significant difference between two corresponding groups, while different lowercase letters indicate significant differences between the two corresponding groups ($p < 0.05$).

The above results indicate that AKK PROBIO may have a therapeutic effect on gouty arthritis at a low dosage, and may have a better therapeutic effect at a high dosage.

The foregoing embodiments are merely used for explaining the technical solutions of the disclosure, but are not intended to limit the disclosure. The substitutions and improvements made by those skilled in the art to conventional means on the basis of the technical solutions disclosed above are within the scope of protection of the disclosure, without departing from the spirit of the disclosure.

What is claimed is:

1. A product comprising a strain of *Akkermansia muciniphila* deposited with the China General Microbiological Culture Collection (CGMCC) having deposit number CGMCC 20955 or a preparation of the strain, together with excipients.

2. The product according to claim 1, wherein the preparation comprises one or more of viable bacteria, dead bacteria, fermented broth, fermented broth precipitates, or freeze-dried powder.

3. The product according to claim 2, wherein the viable bacteria are viable cells obtained from a culture of the strain by centrifugation or filtration.

4. The product according to claim 1, wherein the product is a food, a medicine, a health-care product, a microbial agent, a food additive, a health-care product additive, or a pharmaceutical raw material.

5. The product according to claim 4, wherein the medicine is used for preventing or treating tumors or tumor complications.

6. The product according to claim 5, wherein the tumors comprise solid tumors or non-solid tumor.

7. The product according to claim 6, wherein the solid tumors comprise at least one of motor system tumors, digestive system tumors, respiratory system tumors, nervous system tumors, urinary system tumors, reproductive system tumors, or endocrine system tumors.

8. The product according to claim 7, wherein the tumors comprise any one or more of breast carcinoma, lung carcinoma, colorectal carcinoma, pancreatic carcinoma, or melanoma.

9. The product according to claim 4, wherein the medicine is used for preventing or treating diseases, wherein the diseases comprise at least one of obesity, diabetes, cardiovascular diseases, inflammation, amyotrophic lateral sclerosis, Alzheimer's disease, or complications of at least one of the above diseases.

10. The product according to claim 9, wherein the inflammation comprises acute inflammation or chronic inflammation.

11. The product according to claim 10, wherein the inflammation comprises any one or more of arthritis, gastroenteritis, hepatitis, fasciitis, nephritis, stomatitis, cystitis, pelvic inflammation, cervicitis, keratitis, conjunctivitis, rhinitis, tympanitis, pneumonia, or tracheitis.

12. The product according to claim 4, wherein the medicine is used for preventing or treating a cognitive dysfunction.

13. The product according to claim 4, wherein the health-care product is used for at least one of maintaining intestinal flora balance, maintaining a body shape, maintaining blood pressure, maintaining blood lipids, protecting memory, resisting oxidation, regulating metabolism, or regulating immunity.

14. The product according to claim 4, wherein the product is the medicine, and the medicine further comprises a pharmaceutically acceptable excipient.

15. The product according to claim 14, wherein the pharmaceutically acceptable excipient comprises any one or more of an excipient, a stabilizer, a diluent, an adhesive, a preservative, a lubricant, or an antioxidant.

16. The product according to claim 15, wherein the medicine is in an internal dosage form or external dosage form.

17. The product according to claim 16, wherein the internal dosage form comprises any one of a tablet, powder, a granule, a capsule, oral liquid, pulvis, a pill, syrup, or an effervescing agent.

18. The product according to claim 17, wherein a viable count of the *Akkermansia muciniphila* in the medicine is not less than $1\times10^8$ CFU/g or $1\times10^8$ CFU/mL.

19. The product according to claim 18, wherein the viable count of the *Akkermansia muciniphila* in the medicine is $1\times10^9$ to $1\times10^{12}$ CFU/g or $1\times10^9$ to $1\times10^{12}$ CFU/mL.

20. The product according to claim 1, wherein bacterial cells of the strain are rod-shaped, with a size ranging from 0.5 to 0.9 μm×0.7 to 3.8 μm, arranged singly or in pairs, and Gram-negative, and the strain is sensitive to at least one of ampicillin, ceftriaxone, cefotaxime, meropenem, tetracycline, moxifloxacin, or chloramphenicol.

\* \* \* \* \*